United States Patent
Nagai

(10) Patent No.: US 10,022,093 B2
(45) Date of Patent: Jul. 17, 2018

(54) X-RAY DIAGNOSIS APPARATUS AND CONTROL METHOD

(71) Applicant: Toshiba Medical Systems Corporation, Otawara-shi (JP)

(72) Inventor: Seiichirou Nagai, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 252 days.

(21) Appl. No.: 14/701,143

(22) Filed: Apr. 30, 2015

(65) Prior Publication Data

US 2015/0230763 A1 Aug. 20, 2015

Related U.S. Application Data

(63) Continuation of application No. PCT/JP2013/080700, filed on Nov. 13, 2013.

(30) Foreign Application Priority Data

Nov. 14, 2012 (JP) .................................. 2012-250579

(51) Int. Cl.
*A61B 6/08* (2006.01)
*A61B 6/00* (2006.01)
(Continued)

(52) U.S. Cl.
CPC ................ *A61B 6/08* (2013.01); *A61B 6/487* (2013.01); *A61B 6/54* (2013.01); *F21K 9/56* (2013.01);
(Continued)

(58) Field of Classification Search
CPC .. A61B 6/08; A61B 6/487; A61B 6/54; A61B 6/0457; A61B 6/548; A61B 6/547;
(Continued)

(56) References Cited

U.S. PATENT DOCUMENTS

| 2003/0161441 A1 | 8/2003 | Stevanovic et al. |
| 2004/0131157 A1 | 7/2004 | Stevanovic et al. |

(Continued)

FOREIGN PATENT DOCUMENTS

| JP | 04-200453 A | 7/1992 |
| JP | H08(1996)-238238 | 9/1996 |

(Continued)

OTHER PUBLICATIONS

International Search Report dated Jan. 14, 2014 for PCT/JP2013/080700 filed Nov. 13, 2013 with English Translation.

(Continued)

*Primary Examiner* — Irakli Kiknadze
(74) *Attorney, Agent, or Firm* — Oblon, McClelland, Maier & Neustadt, L.L.P.

(57) ABSTRACT

An X-ray diagnosis apparatus includes an X-ray irradiator, a light source device, and a light emission control unit. The X-ray irradiator emits X-rays to a subject. The light source device includes a light-emitting part and a light irradiation part. The light-emitting part includes a semiconductor laser or a light-emitting diode for emitting light. The light irradiation part emits the light as output light indicating the irradiation field of the X-rays. The light emission control unit controls the light-emitting part according to the operating state of the X-ray irradiator.

17 Claims, 19 Drawing Sheets

(51) Int. Cl.
*F21K 99/00* (2016.01)
*F21V 13/02* (2006.01)
*F21V 23/00* (2015.01)
*F21V 29/70* (2015.01)
*F21V 13/08* (2006.01)
*F21W 131/20* (2006.01)
*F21Y 101/02* (2006.01)

(52) U.S. Cl.
CPC ............... *F21V 13/02* (2013.01); *F21V 13/08* (2013.01); *F21V 23/009* (2013.01); *F21V 29/70* (2015.01); *F21W 2131/20* (2013.01); *F21Y 2101/02* (2013.01); *F21Y 2101/025* (2013.01)

(58) Field of Classification Search
CPC ......... A61B 6/587; A61B 6/4405; A61B 6/06; A61B 6/502; A61B 6/04; A61B 6/588; A61B 6/0492; A61B 6/032; A61B 6/4291; A61B 6/4441; A61B 6/4452; A61B 6/542; A61B 6/583; A61B 6/14; A61B 6/0414; A61B 6/461; A61B 6/02; A61B 6/0407; A61B 6/4411; A61B 6/4464; F21K 9/56; F21V 13/02; F21V 13/08; F21V 23/009; F21V 29/70; F21W 2131/20; F21Y 2101/02; F21Y 2101/025; A61N 2005/105; A61N 5/1049; A61N 5/107; G02B 26/123; G02B 26/0833; G02B 26/10; G02B 26/105; G02B 27/0905; G02B 27/281; G11B 2007/0006; G11B 2007/13727; G11B 7/1275; G11B 7/1353; G11B 7/1369; G11B 7/1374; G11B 7/1376; G11B 7/1378; G11B 7/13922; G11B 7/13925

USPC .................................. 378/62, 145, 206, 207
See application file for complete search history.

(56) References Cited

U.S. PATENT DOCUMENTS

| 2008/0192458 | A1 | 8/2008 | Li | |
| 2009/0190722 | A1* | 7/2009 | Windt | A61B 6/08 378/206 |
| 2011/0199580 | A1* | 8/2011 | Hirata | G03B 21/20 353/31 |

FOREIGN PATENT DOCUMENTS

| JP | 11-111035 A | 4/1999 |
| JP | 11-176220 A | 7/1999 |
| JP | 2001-195904 A | 7/2001 |
| JP | 3084178 U | 3/2002 |
| JP | 2003-265465 A | 9/2003 |
| JP | 2004-209259 A | 7/2004 |
| JP | 2006-192185 A | 7/2006 |
| JP | 2007-200818 | 8/2007 |
| JP | 2007-324085 A | 12/2007 |
| JP | 2008-016314 A | 1/2008 |
| JP | 2008-054749 A | 3/2008 |
| JP | 2008-259881 A | 10/2008 |
| JP | 2010-518587 A | 5/2010 |
| JP | 2011-100739 A | 5/2011 |
| JP | 2011-244873 A | 12/2011 |
| JP | 2013-017630 A | 1/2013 |
| WO | WO 2012/141036 A1 | 10/2012 |

OTHER PUBLICATIONS

Japanese Office Action dated Oct. 17, 2017 in Japanese Patent Application No. 2013-235143.

* cited by examiner

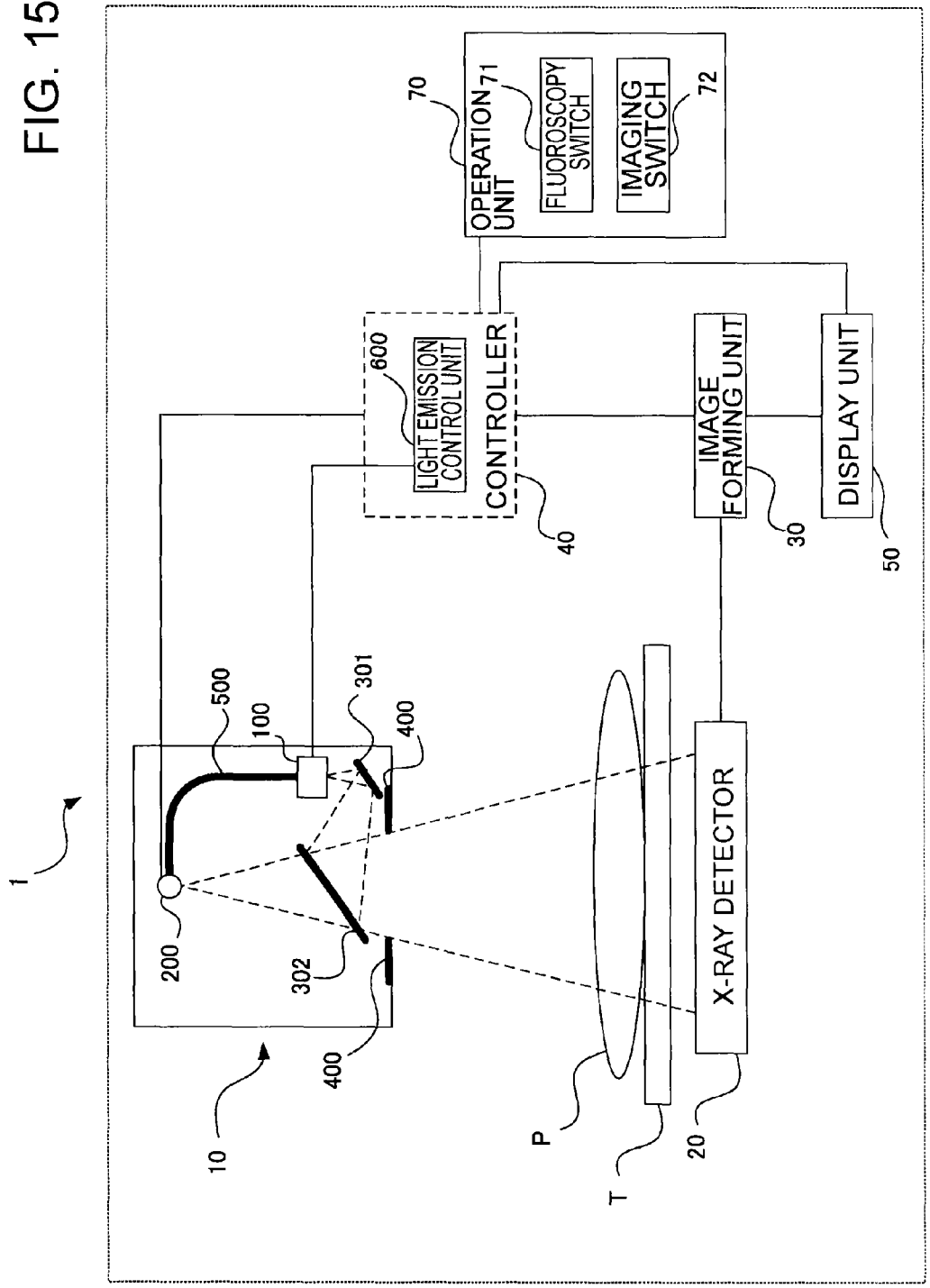

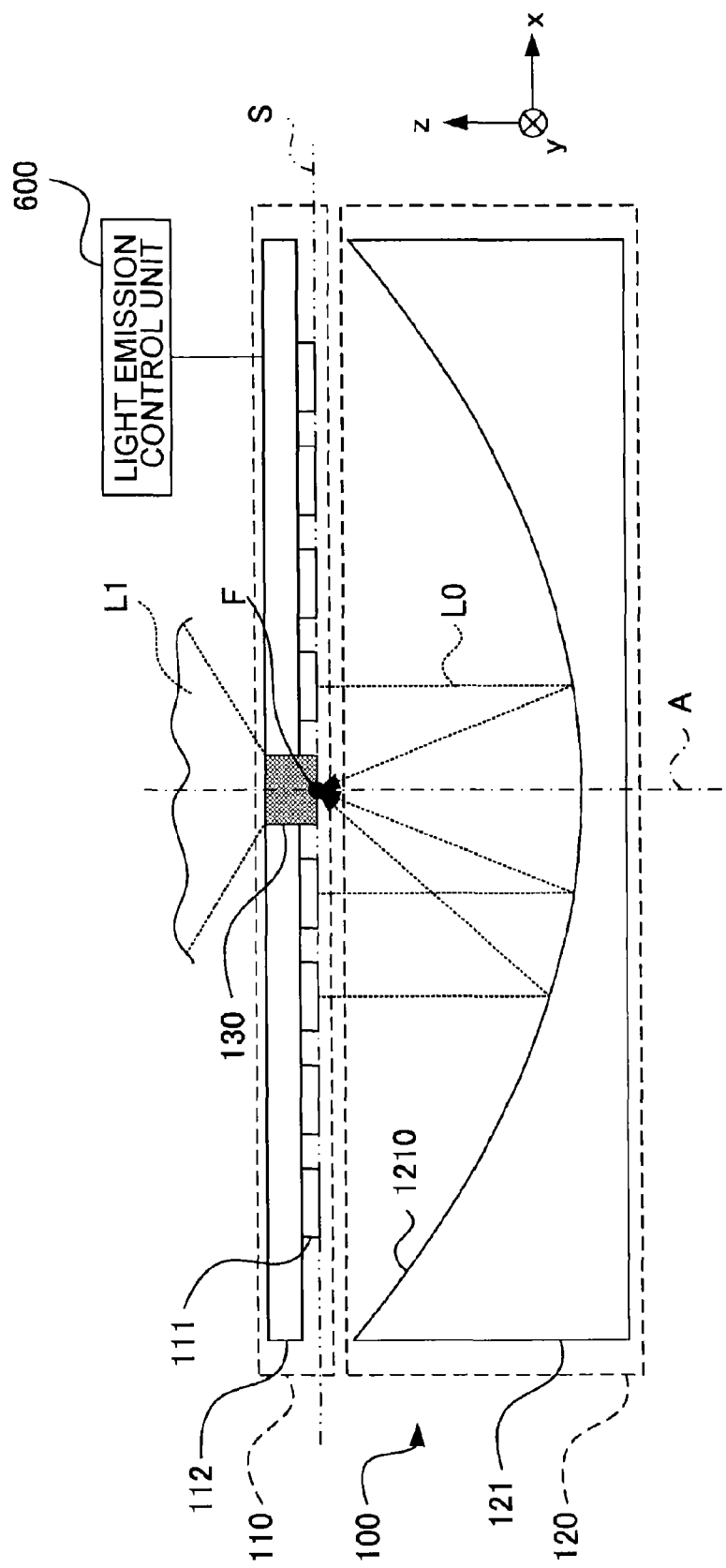

X-RAY DIAGNOSIS APPARATUS AND CONTROL METHOD

CROSS-REFERENCE TO RELATED APPLICATION

This application is based upon and claims the benefit of priority from Japanese Patent Application No. 2012-250579, filed 14 Nov. 2012; the entire contents of which are incorporated herein by reference.

FIELD

Embodiments described herein relate generally to an X-ray diagnosis apparatus and a control method thereof.

BACKGROUND

An X-ray diagnosis apparatus irradiates a subject with X-rays and detects the intensity of X-rays that have passed through the subject to display an image of the internal structure of the subject.

The X-ray diagnosis apparatus is provided with a light source device. In X-ray diagnosis, an operator checks the X-ray irradiation field by visually checking the irradiation field of light from the light source device. The light source device is located in an X-ray irradiation unit such that the optical path of X-rays and that of light emitted therefrom are combined together.

A halogen lamp is used for the conventional light source device. The light source device has a short service life. In addition, although being a light source that simulates an X-ray focal point, the halogen lamp cannot be regarded as a point light source having a sufficiently small light emission point. Therefore, the boundary of the light irradiation field is not clear, and the operator finds it difficult to identify the irradiation field.

Besides, a plurality of light-emitting semiconductors are required to emit light of sufficient brightness when they are used as a substitute for the halogen lamp because of their long service life. However, the plural light-emitting semiconductors do not provide a point light source. Further, the light irradiation field suffers from non-uniform brightness. For these reasons, it is also difficult in this case to identify the irradiation field.

Because of the short service life and poor time response of the halogen lamp, the operator has difficulty in knowing the operating state of the X-ray diagnosis apparatus while viewing the light of the irradiation field.

BRIEF DESCRIPTION OF THE DRAWINGS

FIG. 15 is a view illustrating an example of the configuration of an X-ray diagnosis apparatus according to an embodiment;

FIG. 16B is a view illustrating an example of the configuration of a light source device according to an embodiment;

DETAILED DESCRIPTION

Figure 1:
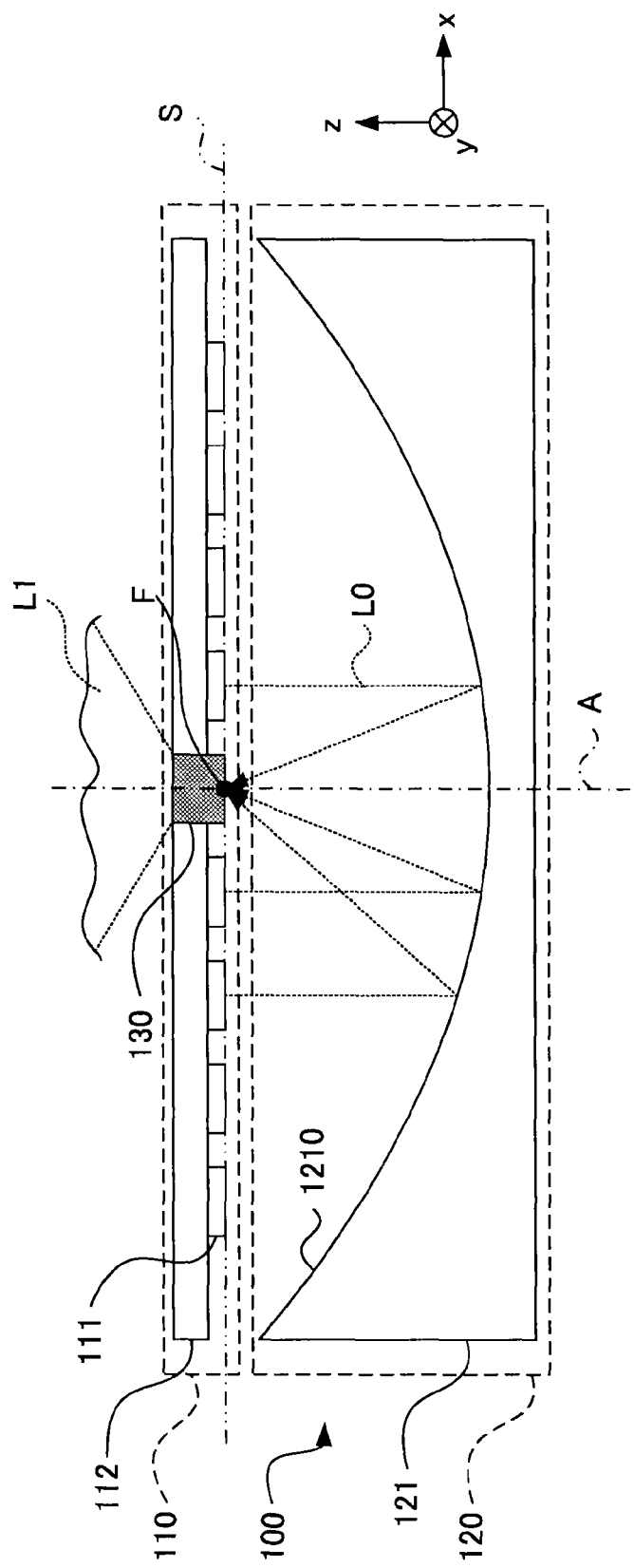
FIG. 1 is a view illustrating an example of the configuration of a light source device according to an embodiment.

In general, according to one embodiment, an X-ray diagnosis apparatus includes an X-ray irradiator, a light source device, and a light emission control unit. The X-ray irradiator emits X-rays to a subject. The light source device includes a light-emitting part and a light irradiation part. The light-emitting part includes a semiconductor laser or a light-emitting diode for emitting light. The light irradiation part emits the light as output light indicating the irradiation field of the X-rays. The light emission control unit controls the light-emitting part according to the operating state of the X-ray irradiator.

Referring now to the drawings, a description is given of a light source device according to embodiments. The light source device described below need not necessarily be used in an X-ray diagnosis apparatus.

First Embodiment of the Light Source Device

[Configuration]

Figure 2:
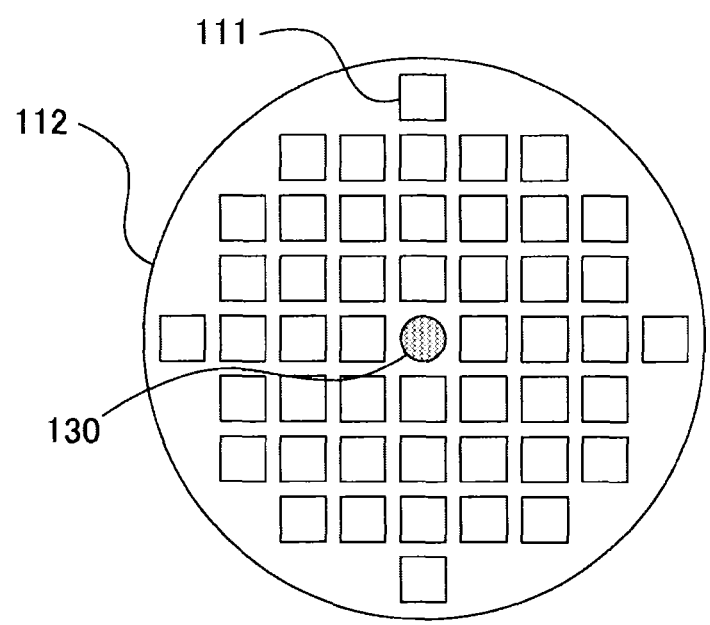
FIG. 2 is a view illustrating an example of the configuration of a light source device according to an embodiment.
Figure 3:
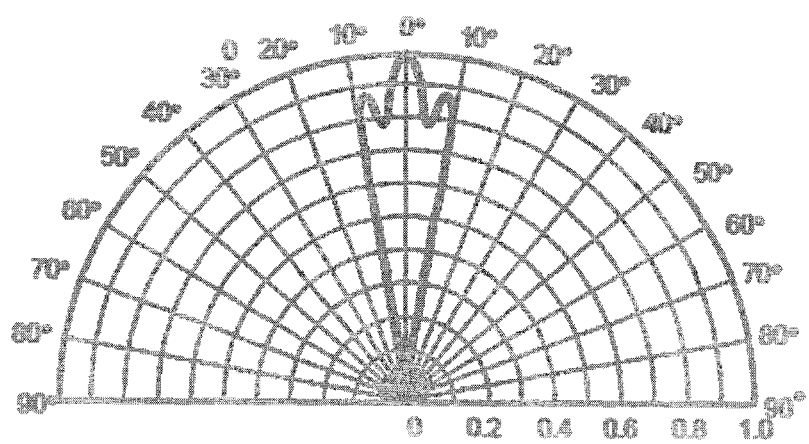
FIG. 3 is a schematic view for explaining a light source device according to an embodiment.

With reference to FIGS. 1 to 3, a description is given of an example of the configuration of a light source device 100 according to one embodiment.

The light source device 100 includes a light-emitting part 110, a reflective part 120, and a light irradiation part 130. The light source device 100 may arbitrarily include a power supply, switches, and the like.

[Light-Emitting Part]

The light-emitting part 110 emits light L0 from its light-emitting surface. The light-emitting part 110 includes a substrate 112 and a plurality of light emitters 111. As illustrated in FIG. 2, the light emitters 111 are arranged on one surface (hereinafter, referred to as "inner surface") of the substrate 112. With this, a light-emitting surface S is formed by the light emitters 111 on the inner surface of the substrate 112. The substrate 112 is a holding substrate for the light emitters 111, and includes a circuit or the like for supplying electric power to the light emitters 111. For example, the light emitters 111 are arranged discretely on the inner surface of the substrate 112. Further, for example, the light emitters 111 are arranged point-symmetrically with respect to the center of the light-emitting surface S of the light-emitting part 110.

The light emitters 111 emit the light L0 having directivity in the normal direction of the light-emitting surface S. A light-emitting semiconductor is used for the light emitters 111. Examples of the light-emitting semiconductor include a so-called bullet light-emitting diode (LED) with narrow emission distribution, a semiconductor laser, and the like. For example, a semiconductor material that emits light as a current flows therethrough is selected for the LED. A semiconductor material that emits laser light is selected for the semiconductor laser. For the LED, a semiconductor material that emits visible light may be selected. If the light irradiation part 130 (described later) includes a fluorescent material, a semiconductor material that emits light having a wavelength that excites the fluorescent material may be selected. For the semiconductor laser, a semiconductor material that emits laser light with a visible light wavelength may be selected. If the light irradiation part 130 (described later) includes a fluorescent material, a semiconductor material that emits laser light having a wavelength that excites the fluorescent material may be selected. In this specification, the light emitted from the light emitters 111 is described as light having a visible light wavelength or light having a wavelength that excites a fluorescent material, or both of them. FIG. 3 illustrates an example of the light emission distribution of a bullet LED. The direction in which the emission intensity is maximum (0° direction in FIG. 3) is referred to as "main beam direction". In FIG. 1, the light-emitting part 110 emits the light L0 mainly in the main beam direction from +z to −z. That is, it can be assumed that as each of the light emitters 111 emits light in the main beam direction, the light-emitting part 110 substantially performs surface emission with directivity from +z to −z.

[Reflective Part]

The reflective part 120 has a reflective surface that collects the light L0 from the light-emitting part 110. The reflective part 120 includes a first reflective part 121 having a parabolic first reflective surface 1210. The first reflective part 121 is arranged such that a focus F of the first reflective surface 1210 is located on the light-emitting surface S, and the axis A of the first reflective surface 1210 is perpendicular to the light-emitting surface S. In FIG. 1, by reflecting the light L0, the first reflective surface 1210 collects the light L0 at the focus F. As described above, the first reflective surface 1210 is formed into a parabolic shape. Besides, the main beam direction is parallel to the axis A. Accordingly, the first reflective surface 1210 reflects the light L0 incident thereon toward the focus F. Thus, the reflective part 120 can collect the light L0 from each of the light emitters 111 at the focus F.

[Light Irradiation Part]

The light irradiation part 130 emits the light L0 as output light indicating the irradiation field of X-rays. The light irradiation part 130 is located at a position including the focus F, and outputs the light L0 collected by the reflective part 120 as output light L1 of uniform brightness. That is, the light irradiation part 130 uniforms the light L0 to output the output light L1. At this time, the light L0 reflected by the first reflective surface 1210 passes through the light irradiation part 130. Examples of constituent elements of the light irradiation part include a diffusion filter that diffuses and outputs the light L0 input thereto, a fluorescent screen including a fluorescent material that, having been excited by the input light L0, emits visible light having a wavelength different from that of the light L0, and the like. Thus, the light irradiation part 130 can output the light L0 from the reflective part 120 as the output light L1 being visible light of uniform brightness by the diffusion of the input light L0, light emission due to excitation, and the like. In this specification, the light emitted from the light irradiation part 130 is described as light in a visible light wavelength. In addition, the output light L1 is described as light having the same wavelength as the light L0 or the light emitted by an excited fluorescent material, or both of them.

[Operation]

Described below is the operation of the light source device 100 in this embodiment.

As each of the light emitters 111 emits the light L0 in the main beam direction, the light-emitting part 110 substantially performs surface emission. The first reflective surface 1210 of the reflective part 120 reflects the light L0 incident thereon toward the focus F. The light irradiation part 130 outputs the light from the reflective part 120 as the output light L1 being visible light of uniform brightness.

The light source device 100 of this embodiment includes the light-emitting part 110, the reflective part 120 and the light irradiation part 130. The light-emitting part 110 emits the light L0 from the light-emitting surface S. The reflective part 120 has a reflective surface, and collects the light L0 from the light-emitting part 110. The light irradiation part 130 outputs the light L0 collected by the reflective part 120 as the output light L1 being visible light of uniform brightness. Accordingly, the surface-emitted light is collected and output as the output light L1 that is visible light of uniform brightness. Thus, it is possible to provide the light source device 100 capable of emitting light of sufficient and uniform brightness.

In this embodiment, the light-emitting part 110 has the light-emitting surface S which is arranged in a plane. The reflective part 120 includes the first reflective part 121 having the parabolic first reflective surface 1210. Thus, it is possible to provide the light source device 100 capable of suitably collecting light from the light-emitting part 110.

Further, in this embodiment, the light irradiation part 130 is arranged to be located at a position where the light L0 is collected. Accordingly, a suitable amount of light is incident on the light irradiation part 130. Thus, it is possible to provide the light source device 100 capable of emitting light of sufficient and uniform brightness.

Further, in this embodiment, the first reflective part 121 is arranged such that the focus F of the first reflective surface 1210 is located on the light-emitting surface S, and the axis A of the first reflective surface 1210 is perpendicular to the light-emitting surface S. The light irradiation part 130 is located substantially at the position of the focus F. Accordingly, the reflective part 120 collects the light from the light-emitting part 110 more suitably, and a further preferred amount of light is incident on the light irradiation part 130. Thus, it is possible to provide the light source device 100 capable of emitting light of sufficient and uniform brightness.

Further, in this embodiment, the light-emitting part 110 may include the light emitters 111 that are arranged discretely. The light emitters 111 may be arranged point-symmetrically with respect to the center of the light-emitting surface S. Besides, in this embodiment, the light emitters 111 can emit the light L0 having directivity in the normal direction of the light-emitting surface S. In addition, in this embodiment, a light-emitting semiconductor can be used for the light emitters 111. With this configuration, it is possible to provide the light source device 100 capable of emitting light of sufficient and uniform brightness.

Further, in this embodiment, the light irradiation part 130 may include a diffusion filter that diffuses and outputs the light L0 collected by the reflective part 120. Thereby, the light L0 incident on the light irradiation part 130 is output as the output light L1 of uniform brightness. Thus, it is possible to provide the light source device 100 capable of emitting light of uniform brightness.

Further, in this embodiment, the light irradiation part 130 may include a fluorescent material that emits light as excited by the light L0 collected by the reflective part 120. With this, the light irradiation part 130 outputs the output light L1 being visible light of uniform brightness. Thus, it is possible to provide the light source device 100 capable of emitting light of uniform brightness.

Second Embodiment of the Light Source Device

[Configuration]

Figure 4:
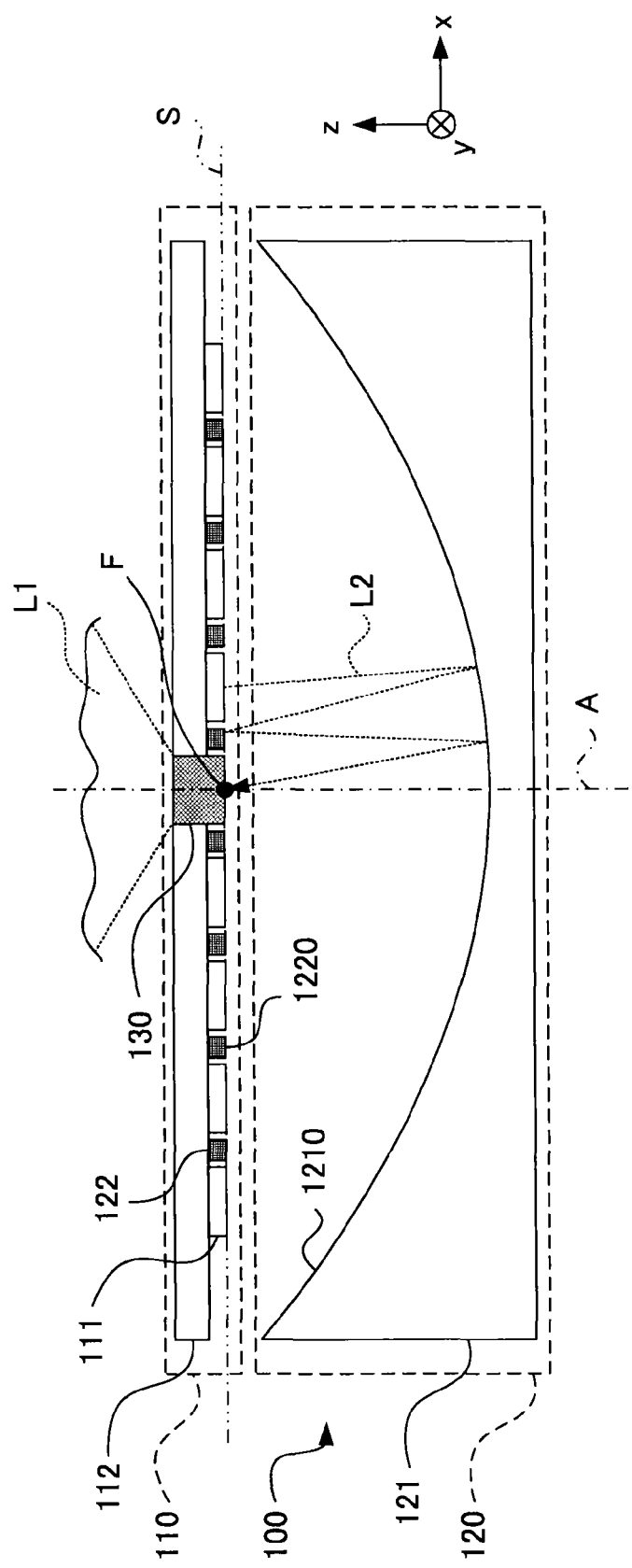
FIG. 4 is a view illustrating an example of the configuration of a light source device according to an embodiment.

In the light source device 100 of this embodiment, the reflective part 120 includes a second reflective part 122. FIG. 4 is a schematic diagram illustrating an example of the configuration of the light source device 100 of the embodiment. The second reflective part 122 is located between an adjacent pair of the light emitters 111. The second reflective part 122 has a planar second reflective surface 1220 arranged substantially in the same plane as the light-emitting surface S. The second reflective surface 1220 reflects light L2 not incident on the light irradiation part 130 among light reflected by the first reflective surface 1210. The light L2 is generated by the light emission distribution and the like of the light emitters 111 as well as the tolerance of the first light emitters 111, the substrate 112, and the first reflective surface 1210. The light L2 is repeatedly reflected on the first reflective surface 1210 and the second reflective surface 1220, and is incident on the light irradiation part 130.

Figure 5:
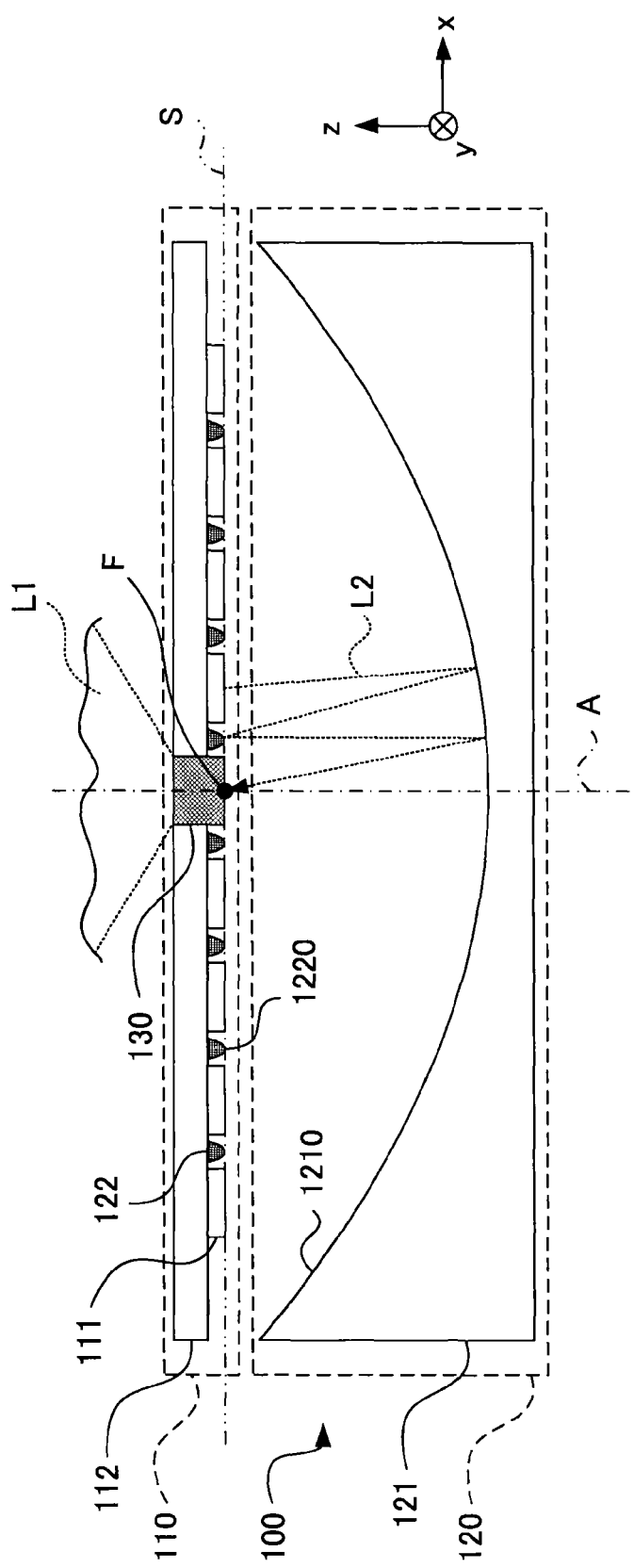
FIG. 5 is a view illustrating an example of the configuration of a light source device according to an embodiment.

As illustrated in FIG. 5, the second reflective part 122 may have the second reflective surface 1220, at least part of which is formed in a curved shape. The light L2 is repeatedly reflected on the first reflective surface 1210 and the second reflective surface 1220, and is incident on the light irradiation part 130.

Figure 6:
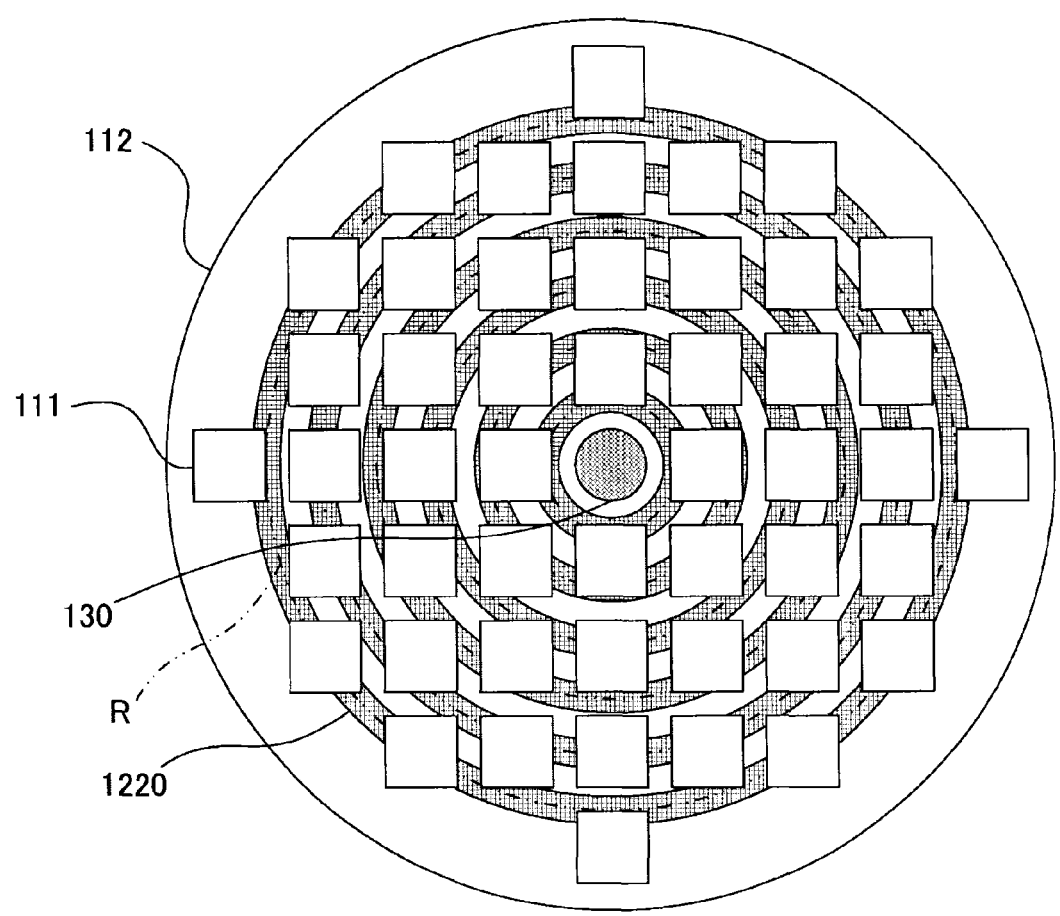
FIG. 6 is a view illustrating an example of the configuration of a light source device according to an embodiment.

Further, as illustrated in FIG. 6, the second reflective surface 1220 may be formed in a concave-convex shape having ridges R in concentric circles. The light L2 is repeatedly reflected on the first reflective surface 1210 and the second reflective surface 1220, and is incident on the light irradiation part 130.

[Operation]

Described below is the operation of the light source device 100 in this embodiment.

The first reflective surface 1210 reflects light from the light emitters 111. The second reflective surface 1220 reflects the light L2 not incident on the light irradiation part 130 in the reflected light. The light L2 is repeatedly reflected on the first reflective surface 1210 and the second reflective surface 1220, and is incident on the light irradiation part 130.

In this embodiment, the reflective part 120 includes the second reflective part 122. The second reflective part 122 is located between an adjacent pair of the light emitters 111. The second reflective part 122 has the second reflective surface 1220. The second reflective surface 1220 reflects the light L2 not incident on the light irradiation part 130 among light reflected by the first reflective surface 1210. The light L2 is repeatedly reflected on the first reflective surface 1210 and the second reflective surface 1220, and is incident on the light irradiation part 130. Thus, it is possible to provide a light source device capable of emitting light of suitable brightness.

In this embodiment, the second reflective part 122 may have the planar second reflective surface 1220 arranged substantially in the same plane as the light-emitting surface S. Thus, it is possible to provide a light source device capable of emitting light of further suitable brightness.

Further, in this embodiment, the second reflective part 122 may have the second reflective surface 1220, at least part of which is formed in a curved shape. Thus, it is possible to provide a light source device capable of emitting light of further suitable brightness.

Further, in this embodiment, the second reflective surface 1220 may have ridges R in concentric circles. Thus, it is possible to provide a light source device capable of emitting light of further suitable brightness.

Third Embodiment of the Light Source Device

[Configuration]

The light source device 100 of this embodiment further includes a heat radiation part. The heat radiation part radiates heat generated by the light emitters 111 of the light-emitting part 110, the power supply wiring of the substrate 112, and the like.

Figure 7:
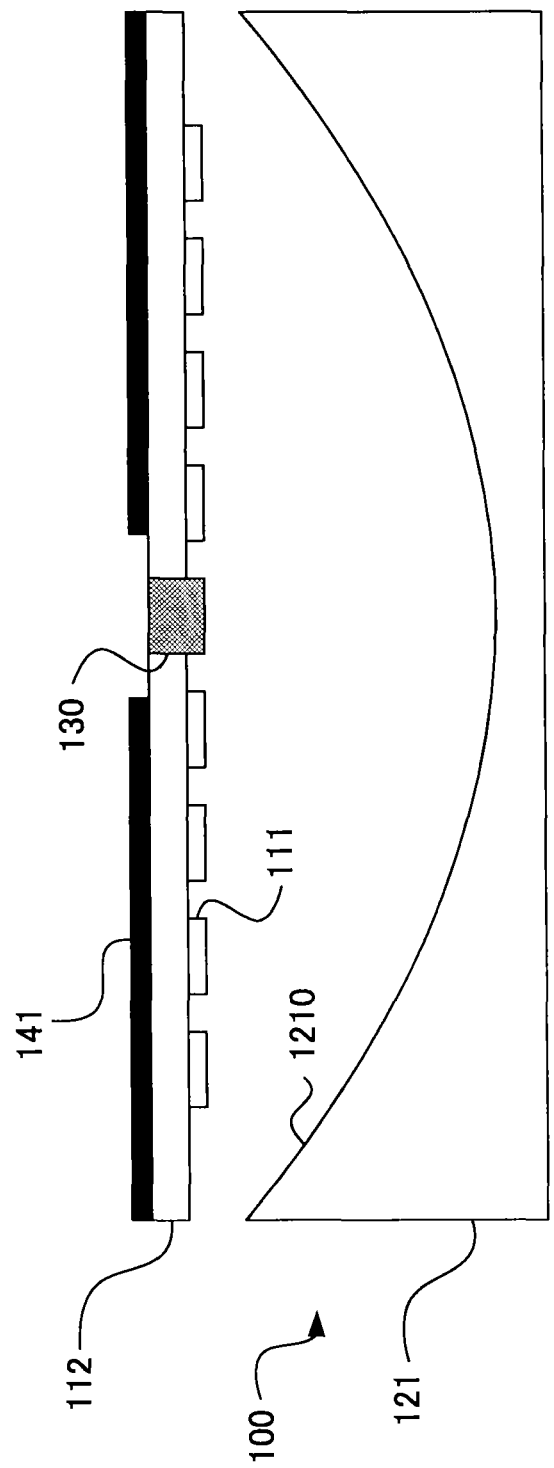
FIG. 7 is a view illustrating an example of the configuration of a light source device according to an embodiment.

As illustrated in FIG. 7, the light source device 100 may include a first heat radiation part 141 as the heat radiation part. The first heat radiation part 141 is located on a side of the substrate 112 of the light-emitting part 110 opposite to the side with the light emitters 111. In other words, the first heat radiation part 141 is provided on a side of the substrate 112 of the light-emitting part 110 opposite to the light-emitting surface S. For example, the first heat radiation part 141 may be formed of a coating suitable for heat radiation, a heat radiation member such as a heat sink, a path of a cooling medium, and the like. The surface provided with the first heat radiation part 141 is referred to as the outer surface of the substrate 112.

Figure 8:
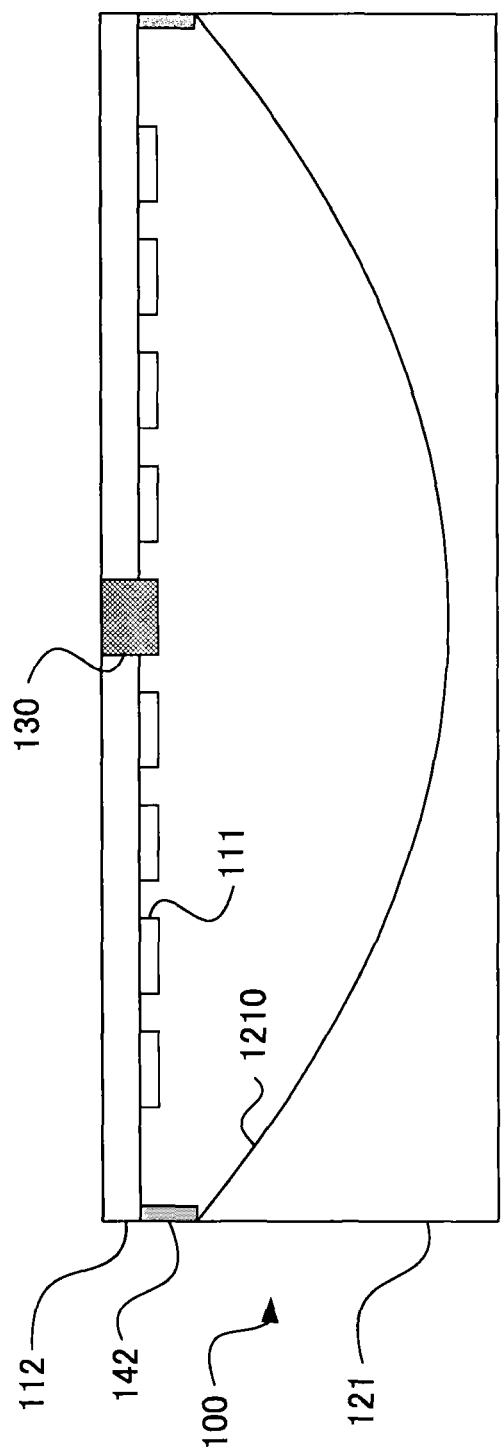
FIG. 8 is a view illustrating an example of the configuration of a light source device according to an embodiment.

As illustrated in FIG. 8, the light source device 100 may further include a second heat radiation part 142 as the heat radiation part. The second heat radiation part 142 is located between the outer edge of the light-emitting part 110 and the outer edge of the first reflective part 121. The second heat radiation part 142 may be formed of, for example, a member having a cavity such as a punching metal, a heat radiation member such as a cooling fan, a heat sink, and the like.

The light source device 100 may further include a third heat radiation part 143 as the heat radiation part. The third heat radiation part 143 radiates heat through the reflective part 120. For example, the third heat radiation part 143 may form the first reflective surface 1210 in one surface of a metal member having high thermal conductivity, and have the functions of the first reflective part 121. Besides, the third heat radiation part 143 may form the second reflective surface 1220 in one surface of a metal member having high thermal conductivity, and have the functions of the second reflective part 122.

The third heat radiation part 143 may be formed as part of the reflective part 120. In this case, the third heat radiation part 143 may be formed of a plurality of members that are arranged in point symmetry. With this, while the reflective part 120 suitably collects light from the light-emitting part 110, the third heat radiation part 143 can radiate heat from the light-emitting part 110.

Figure 9:
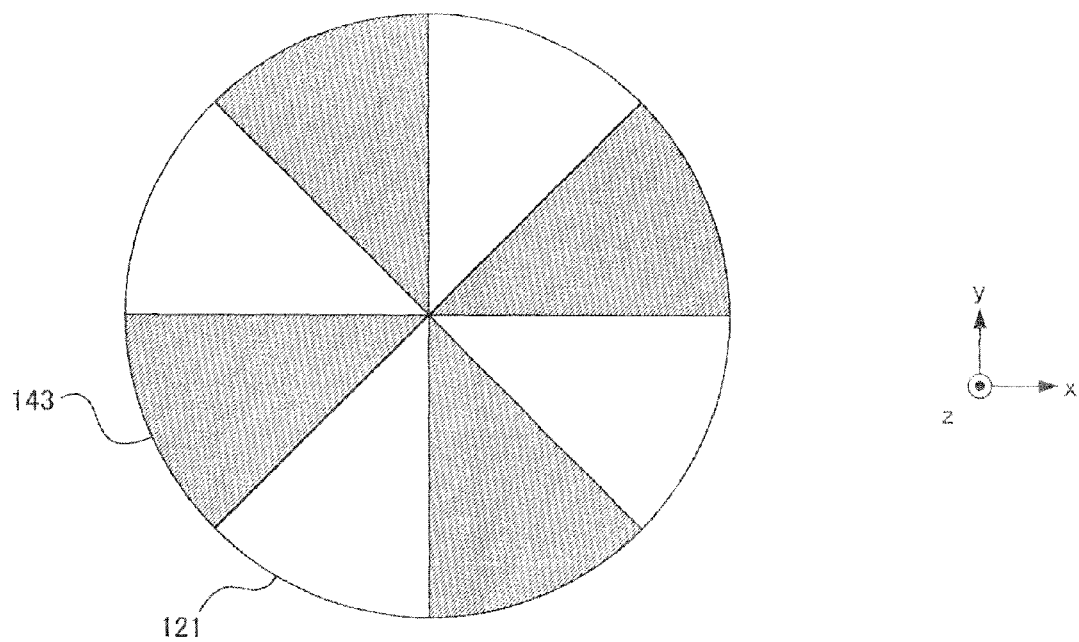
FIG. 9 is a view illustrating an example of the configuration of a light source device according to an embodiment.
Figure 10:
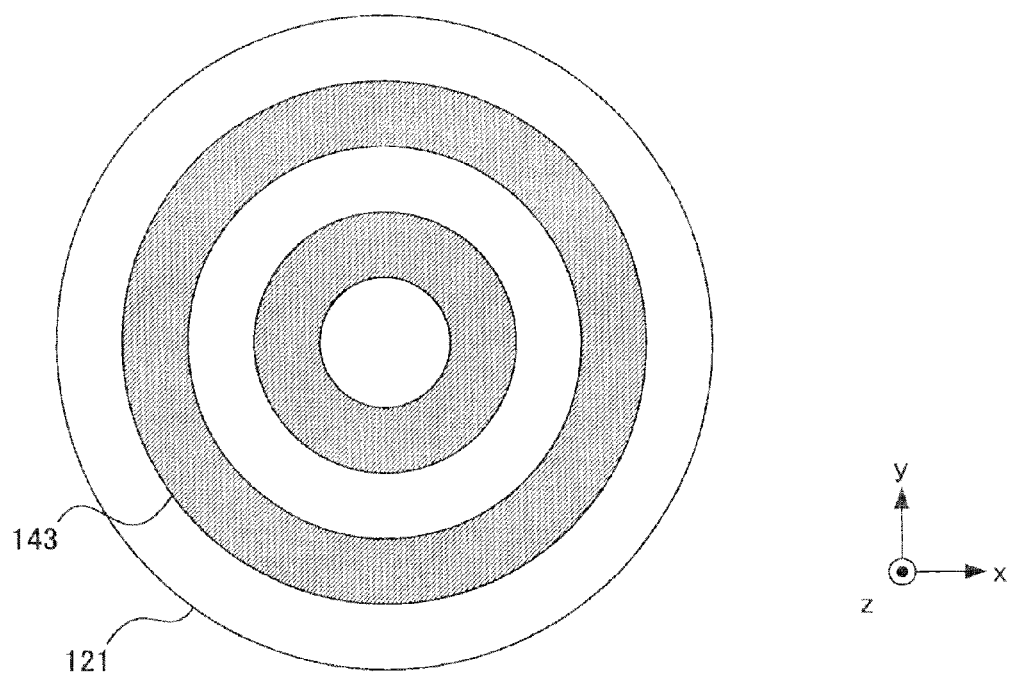
FIG. 10 is a view illustrating an example of the configuration of a light source device according to an embodiment.

FIG. 9 is a diagram illustrating an example of the third heat radiation part 143 formed as part of the first reflective part 121. FIG. 9 illustrates the first reflective part 121 viewed from the +z side towards the −z direction. As illustrated in FIG. 9, each of the members that constitute the third heat radiation part 143 may be formed substantially in a fan shape. FIG. 10 is a diagram illustrating another example of the third heat radiation part 143 formed as part of the first reflective part 121. FIG. 10 illustrates the first reflective part 121 viewed from the +z side towards the −z direction. As illustrated in FIG. 10, the members that constitute the third heat radiation part 143 may be arranged concentrically. The third heat radiation part may be formed of, for example, a coating suitable for heat radiation, a member having a cavity such as a punching metal, a heat radiation member such as a heat sink, and the like. The third heat radiation part 143 may be formed as part of the second reflective part 122.

[Operation]

Described below is the operation of the light source device 100 in this embodiment.

When the light-emitting part 110 emits light, heat is generated from the light emitters 111, the power supply wiring of the substrate 112, and the like. The first heat radiation part 141 radiates the heat from the outer surface of the substrate 112. The second heat radiation part 142 and the third heat radiation part 143 radiate heat that may be retained between the light-emitting part and the first reflective part 121.

In this embodiment, the light source device 100 further includes the first heat radiation part 141 on a side opposite to the light-emitting surface S in the light-emitting part 110. The first heat radiation part 141 radiates heat generated by the light emitters 111, the power supply wiring of the substrate 112, and the like from the outer surface of the substrate 112. Thus, it is possible to provide a light source device reducing adverse effects such as the deformation and deterioration of the members due to heat generation.

Further, in this embodiment, the light source device 100 may further include the second heat radiation part 142 that is located between the outer edge of the light-emitting part 110 and the outer edge of the first reflective part 121. The second heat radiation part 142 radiates heat that may be retained between the light-emitting part 110 and the reflective part 120. Thus, it is possible to provide a light source device reducing adverse effects such as the deformation and deterioration of the members due to heat generation.

Further, in this embodiment, the light source device 100 may further include the third heat radiation part 143 that radiates heat through the first reflective part 121. The third heat radiation part 143 radiates heat that may be retained between the light-emitting part 110 and the reflective part 120. Thus, it is possible to provide a light source device reducing adverse effects such as the deformation and deterioration of the members due to heat generation.

Further, in this embodiment, the third heat radiation part 143 may be formed as part of the first reflective part 121. Thus, it is possible to provide a light source device capable of preferably radiating heat that may be retained between the light-emitting part 110 and the reflective part 120.

Further, in this embodiment, the third heat radiation part 143 may be formed of a plurality of members that are arranged in point symmetry. In this case, each of the members may be formed substantially in a fan shape. With this, it is possible to provide a light source device, in which, while the reflective part 120 suitably collects light from the light-emitting part 110, the third heat radiation part 143 can radiate heat from the light-emitting part 110.

Further, in this embodiment, the members of the third heat radiation part 143 may be arranged concentrically. With this, it is possible to provide a light source device, in which, while the reflective part 120 suitably collects light from the light-emitting part 110, the third heat radiation part 143 can radiate heat from the light-emitting part 110.

Fourth Embodiment of the Light Source Device

[Configuration]

Figure 11:
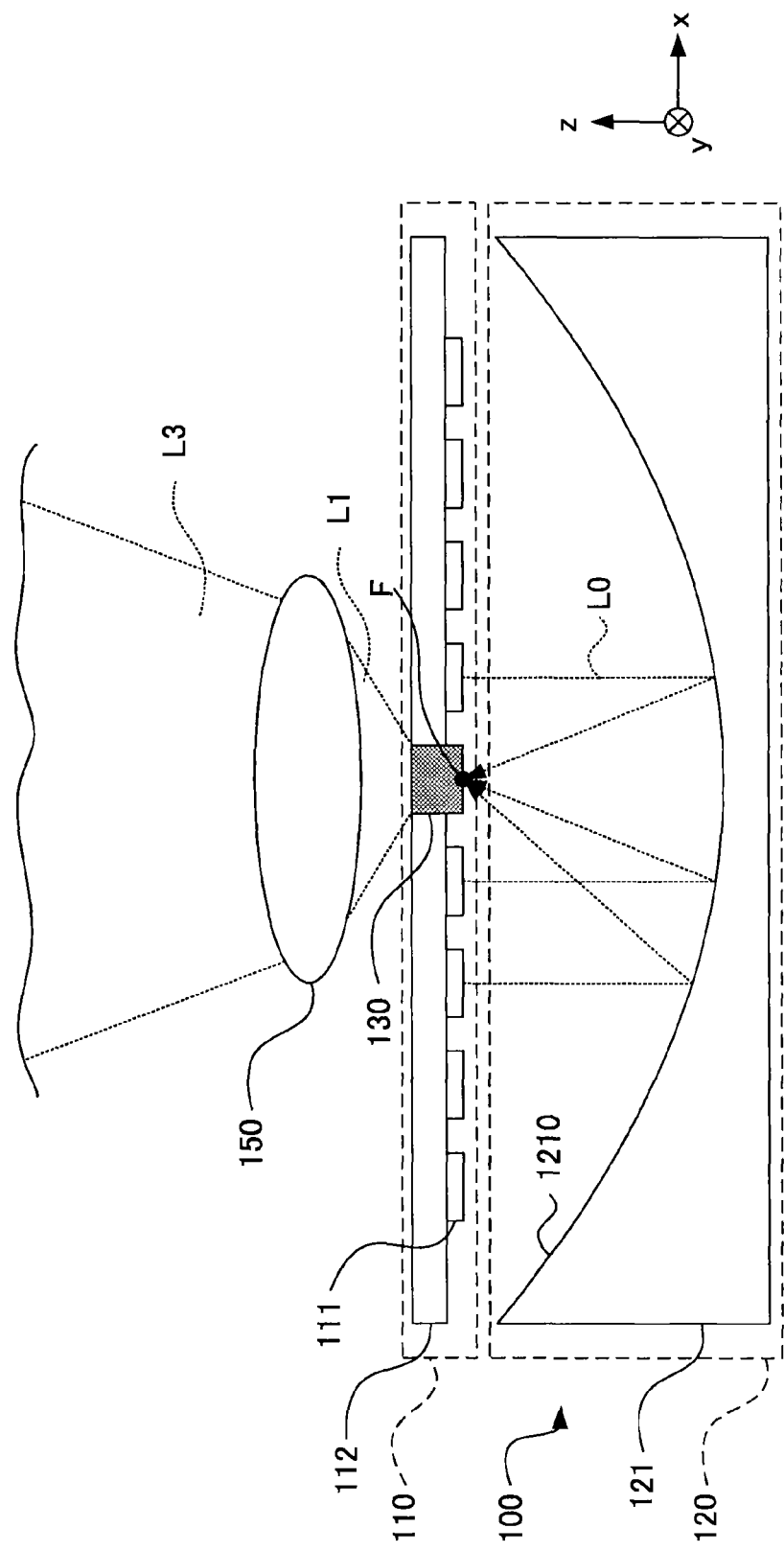
FIG. 11 is a view illustrating an example of the configuration of a light source device according to an embodiment.

The light source device 100 of this embodiment is described with reference to FIG. 11.

The light source device 100 includes a positive lens 150 in the subsequent stage of the light irradiation part 130. The subsequent stage refers to a downstream of the optical path of light from the light-emitting part 110. The positive lens 150 emits the output light L1 from the light irradiation part 130 as output light L3 with a spread angle smaller than that of the output light L1.

[Operation]

The light-emitting part 110 emits the light L0. The reflective part 120 collects light by reflecting the light L0. The light irradiation part 130 emits the light from the reflective part 120 as the output light L1. The positive lens 150 suppresses the spread angle of the output light L1, and emits the light L1 as the output light L3.

In this embodiment, the light source device 100 includes the positive lens 150 in the subsequent stage of the light irradiation part 130. The positive lens 150 suppresses the spread angle of the output light L1, and emits the light L1 as the output light L3. Thus, it is possible to provide the light source device 100 capable of emitting light of sufficient and uniform brightness.

Embodiment of the X-Ray Irradiation Unit

[Configuration]

Figure 12:
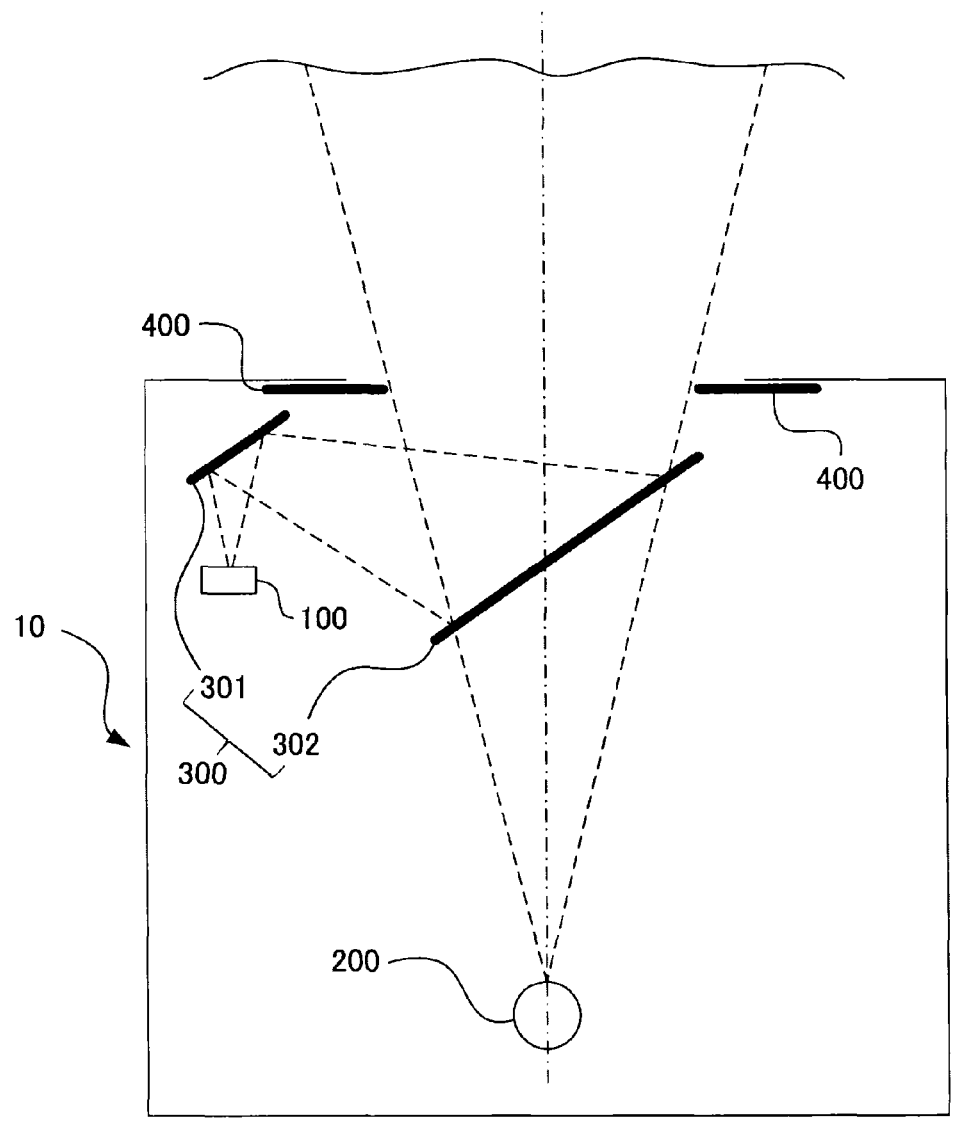
FIG. 12 is a view illustrating an example of the configuration of an X-ray irradiation unit according to an embodiment.

Referring to FIG. 12, a description is given of an example of the configuration of an X-ray irradiation unit 10 of one embodiment.

The X-ray irradiation unit 10 emits visible light and X-rays to a subject. The X-ray irradiation unit 10 includes the light source device 100, an X-ray generator 200, an optical path combining unit 300, and an irradiation field limiter 400. The light source device of any one of the first to fifth embodiments can be used as the light source device 100 (the fifth embodiment of the light source device is described later). The X-ray irradiation unit corresponds to an example of "X-ray irradiator".

The light source device 100 emits light of sufficient and uniform brightness. The light source device 100 includes the light-emitting part 110, the reflective part 120, and the light irradiation part 130. The light-emitting part 110 emits light from the light-emitting surface S. The reflective part 120 has a reflective surface, and collects the light from the light-emitting part 110. The light irradiation part 130 outputs the light collected by the reflective part 120 as output light of uniform brightness.

The X-ray generator 200 generates X-rays. The X-ray generator 200 includes an X-ray tube. The X-ray tube is a vacuum tube that generates X-rays. The X-ray generator 200 supplies a heating current to the filament (cathode) of the X-ray tube to make it emit electrons, and applies a high voltage between the filament and the tungsten (anode) to accelerate the electrons so that the electrons collide with the tungsten (anode). X-rays are generated when the electrons are accelerated and collide with the tungsten anode.

The optical path combining unit 300 coaxially combines the optical path of light emitted from the light source device 100 with the optical path of X-rays from the X-ray generator 200. The optical path combining unit 300 includes a first mirror 301 and a second mirror 302. The irradiation field limiter 400 includes an opaque shielding plate for visible light and X-rays, and limits the irradiation field of light emitted from the light source device 100 and the irradiation field of X-rays from the X-ray generator 200 according to the opening.

The first mirror 301 reflects light emitted from the light source device 100. The second mirror 302 reflects the light reflected by the first mirror 301, and transmits X-rays from the X-ray generator 200. The first mirror 301 and the second mirror 302 are arranged such that the optical path of the light reflected by the second mirror 302 and that of the X-rays having passed through the second mirror 302 are combined coaxially. Besides, both the light irradiation part 130 of the light source device 100 and the X-ray tube of the X-ray generator 200 are a substantially point light source, and arranged at equivalent positions on the optical paths coaxially combined as described above. With this, the X-ray irradiation unit 10 has a configuration in which the light irradiation part 130 emits light indicating the irradiation field of X-rays.

[Operation]

The light source device 100 emits light of sufficient and uniform brightness. The first mirror 301 reflects light emitted from the light source device 100. The second mirror 302 reflects the light reflected by the first mirror 301. The optical path of the light reflected by the second mirror 302 is combined coaxially with the optical path of X-rays from the X-ray generator 200. The X-ray generator 200 generates X-rays. Having passed through the second mirror 302, the X-rays are emitted via the optical path coaxial with the optical path of the light reflected by the second mirror 302. The irradiation field limiter 400 limits the irradiation fields of light emitted from the light source device 100 and X-rays from the X-ray generator 200 to the same range by an opaque shielding plate for visible light and X-rays.

In this embodiment, the X-ray irradiation unit 10 includes the light source device 100, the X-ray generator 200, and the optical path combining unit 300. The light source device 100 outputs the output light of uniform brightness. The light source device 100 includes the light-emitting part 110, the reflective part 120, and the light irradiation part 130. The light-emitting part 110 emits light from the light-emitting surface S. The reflective part 120 has a reflective surface, and collects light from the light-emitting part 110. The light irradiation part 130 outputs the light collected by the reflective part 120 as output light being visible light of uniform brightness. The X-ray generator 200 generates X-rays. The optical path combining unit 300 coaxially combines the optical path of the output light with the optical path of the X-rays. The irradiation field limiter 400 limits the irradiation fields of light emitted from the light source device 100 and X-rays from the X-ray generator 200 to the same range. Thus, it is possible to provide an X-ray irradiating unit capable of emitting light of sufficient and uniform brightness and also emitting X-rays in the same irradiation field as that of the light.

Modification of the X-Ray Irradiation Unit

[Configuration]

Figure 13:
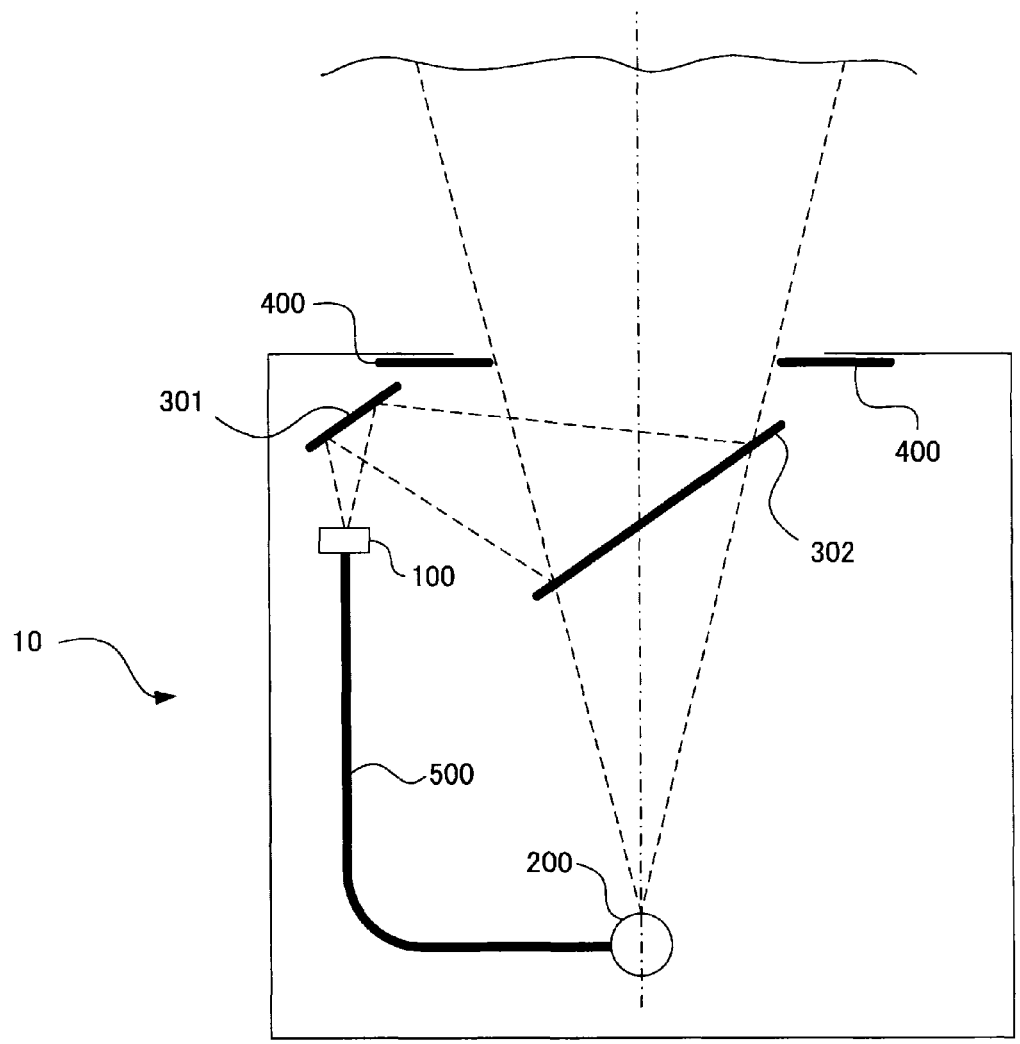
FIG. 13 is a view illustrating an example of the configuration of an X-ray irradiation unit according to an embodiment.

As illustrated in FIG. 13, in this embodiment, the X-ray irradiation unit 10 includes a heat radiation part 500 that thermally connects the light source device 100 to the X-ray generator 200. The heat radiation part 500 radiates heat from the light source device 100 and the X-ray generator 200. The heat radiation part 500 may be formed of a heat radiation member such as a heat sink, a path of a cooling medium, and the like.

In this embodiment, the X-ray irradiation unit 10 includes the heat radiation part 500 that thermally connects the light source device 100 to the X-ray generator 200. Thus, it is possible to provide an X-ray irradiation unit capable of suitably radiating heat generated by the light source device 100 and the X-ray generator 200.

Embodiment of the X-Ray Diagnosis Apparatus

[Configuration]

Figure 14:
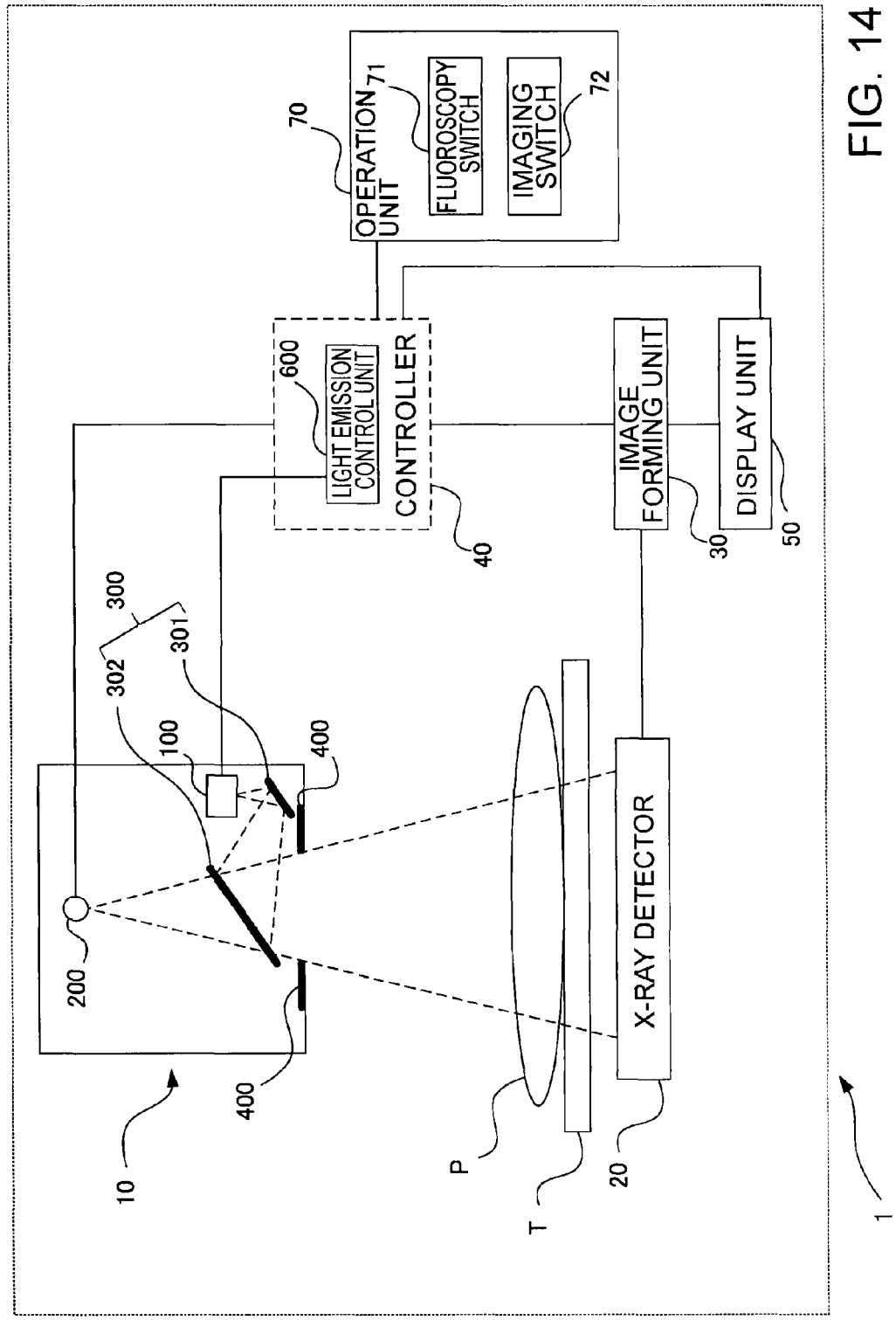
FIG. 14 is a view illustrating an example of the configuration of an X-ray diagnosis apparatus according to an embodiment.

Referring to FIG. 14, a description is given of an example of the configuration of an X-ray diagnosis apparatus 1 according to one embodiment.

The X-ray diagnosis apparatus 1 includes the X-ray irradiation unit 10, an X-ray detector 20, an image forming unit 30, a controller 40, a display unit 50, and an operation unit 70. Having irradiated a subject P with X-rays, the X-ray diagnosis apparatus 1 detects X-rays that have passed through the subject P, thereby performing X-ray fluoroscopy or X-ray imaging. In X-ray fluoroscopy, generally, the subject P is continuously irradiated with X-rays at a lower dose than in X-ray imaging, and X-ray fluoroscopic images are sequentially displayed on the display unit at regular intervals (frame rate). Generally, in X-ray imaging, the subject P is irradiated with X-rays at a higher dose and for a shorter time than in X-ray fluoroscopy to form an X-ray image at a higher resolution than the X-ray fluoroscopic images.

The X-ray irradiation unit 10 emits visible light and X-rays to the subject P. The X-ray irradiation unit 10 includes the light source device 100, the X-ray generator 200, the optical path combining unit 300, and the irradiation field limiter 400. In the X-ray irradiation unit 10, the conditions of X-ray irradiation vary according to its operating state. The operating state includes stopped state, fluoroscopy state, and imaging state. The stopped state refers to a state in which X-ray irradiation is stopped. The fluoroscopy state refers to a state in which the X-rays for X-ray fluoroscopy are irradiated. The imaging state refers to a state in which X-rays for X-ray imaging are irradiated. The light source device of any one of the first to fifth embodiments can be used as the light source device 100 (the fifth embodiment of the light source device is described later).

The light source device 100 emits light of sufficient and uniform brightness. The light source device 100 includes the light-emitting part 110, the reflective part 120, and the light irradiation part 130. The light-emitting part 110 emits light from the light-emitting surface S. The reflective part 120 has a reflective surface, and collects the light from the light-emitting part 110. The light irradiation part 130 outputs the light collected by the reflective part 120 as output light being visible light of uniform brightness.

The X-ray generator 200 generates X-rays. The X-ray generator 200 includes an X-ray tube. The X-ray tube is a vacuum tube that generates X-rays. The X-ray generator 200 supplies a heating current to the filament (cathode) of the X-ray tube to make it emit electrons, and applies a high voltage between the filament and the tungsten (anode) to accelerate the electrons so that the electrons collide with the tungsten (anode). X-rays are generated when the electrons are accelerated and collide with the tungsten anode.

The optical path combining unit 300 coaxially combines the optical path of light emitted from the light source device 100 with the optical path of X-rays from the X-ray generator 200. The optical path combining unit 300 includes the first mirror 301 and the second mirror 302.

The first mirror 301 reflects light emitted from the light source device 100. The second mirror 302 reflects the light reflected by the first mirror 301, and transmits X-rays from the X-ray generator 200. The first mirror 301 and the second mirror 302 are arranged such that the optical path of the light reflected by the second mirror 302 and that of the X-rays having passed through the second mirror 302 are combined coaxially.

The irradiation field limiter 400 limits the irradiation field of light emitted from the light source device 100 and the irradiation field of X-rays from the X-ray generator 200 to the same range. An operator checks the irradiation field with the light from the light source device 100 prior to the generation of X-rays.

The X-ray detector 20 detects X-rays having passed through the subject P and outputs detection data. The X-ray detector 20 is formed of, for example, an image intensifier, an X-ray flat panel detector, and the like. A platform T is used for supporting the subject P, and is formed of a member that transmits X-rays therethrough.

As well as converting X-rays into light on the phosphor screen of scintillator or the like and emitting photoelectrons from the photoelectric surface which is made in contact with the phosphor screen, the image intensifier focuses and accelerates the electrons by an electron lens made of the focusing electrode and the anode, and thereby forms an electron image on the output phosphor screen. Further, the image intensifier converts the electron image into a visible image on the output phosphor screen and photographs it with a camera to acquire image data (detection data).

The X-ray flat panel detector has a detection surface including multiple rows and columns of X-ray detection elements arranged thereon. As the X-ray detection elements, those of indirect conversion type that convert X-rays into light with a fluorescent material such as scintillator and then convert the light into electric charge by a photoelectric conversion element such as a photodiode light, and those of direct conversion type using the formation of electron hole pairs in a semiconductor by X-rays and their transfer to the electrodes (i.e., photoconductive phenomenon) may be used. The X-ray flat panel detector forms charge data (detection data) corresponding to the X-ray dose.

The X-ray flat panel detector is adapted to read out the charge in device units according to the sequence of the X-ray detection elements. The detection data output from each element includes coordinate information of the element in the two-dimensional coordinate system based on two-dimensional element arrangement.

The image forming unit 30 forms an image (X-ray image) representing the internal structure of the subject P based on the detection data from the X-ray detector 20. The image forming unit 30 includes a computer that functions to convert the detection data output from the X-ray detector 20 to a digital signal and perform various types of image processing to form an image (image data).

The controller 40 controls the operation of each unit of the X-ray diagnosis apparatus 1. The controller 40 includes a microprocessor such as a central processing unit (CPU), a storage device (a memory, a hard disk drive, etc.) that stores various types of data and a predetermined computer program, and the like. The microprocessor performs control related to this embodiment by executing the computer program.

The display unit 50 includes a display device of any form such as a cathode ray tube (CRT) display, a liquid crystal display (LCD), or the like. The display unit 50 displays various images under the control of the controller 40.

The operation unit 70 is used by the operator to input various instructions and information to the X-ray diagnosis apparatus 1. For example, the operation unit 70 is configured to be capable of receiving operation related to the operating state of the X-ray irradiation unit 10. The operation unit 70 includes a fluoroscopy switch 71 and an imaging switch 72. The fluoroscopy switch 71 receives the operation to start or stop the fluoroscopy state. The imaging switch 72 receives the operation to start or stop the imaging state. The operation unit 70 includes a foot switch, a hand switch, and the like. For example, in the operation unit 70, the fluoroscopy switch 71 and the imaging switch 72 are each assigned to a predetermined pedal of the foot switch or a hand switch. This configuration allows the operator to perform operation to start or stop the fluoroscopy state and the imaging state using the operation unit 70.

[Operation]

The X-ray irradiation unit 10 emits visible light to the subject P. The light source device 100 emits light of sufficient and uniform brightness. The light is irradiated onto the subject P via the optical path combining unit 300. The X-ray generator 200 generates X-rays. The X-rays are irradiated onto the subject P. At this time, since the optical path of the light and that of the X-rays are coaxial, the irradiation field of the light and that of the X-rays are in the same range.

The X-ray detector 20 detects X-rays that have passed through the subject P, and outputs detection data. The image forming unit 30 forms an image (X-ray image) representing the internal structure of the subject P based on the detection data from the X-ray detector 20. The image thus formed is displayed on the display unit 50.

In this embodiment, the X-ray diagnosis apparatus 1 includes the X-ray irradiation unit 10, the X-ray detector 20, and the image forming unit 30. The X-ray irradiation unit 10 irradiates the subject P with visible light and X-rays. The X-ray irradiation unit 10 includes the light source device 100, the X-ray generator 200, the optical path combining unit 300, and the irradiation field limiter 400. The light source device 100 emits light of sufficient and uniform brightness. The light source device 100 includes the light-emitting part 110, the reflective part 120, and the light irradiation part 130. The light-emitting part 110 emits light from the light-emitting surface S. The reflective part 120 has a reflective surface, and collects the light from the light-emitting part 110. The light irradiation part 130 outputs the light collected by the reflective part 120 as output light being visible light of uniform brightness. The X-ray generator 200 generates X-rays. The optical path combining unit 300 coaxially combines the optical path of light emitted from the light source device 100 with the optical path of X-rays from the X-ray generator 200. The irradiation field limiter 400 limits the irradiation field of light emitted from the light source device 100 and that of X-rays from the X-ray generator 200 to the same range. The X-ray detector 20 detects X-rays that have passed through the subject P, and outputs detection data. The image forming unit 30 forms an image (X-ray image) representing the internal structure of the subject P based on the detection data from the X-ray detector 20. Thus, it is possible to provide an X-ray diagnosis apparatus capable of emitting light of sufficient and uniform brightness and also performing X-ray diagnosis while emitting X-rays in the same irradiation field as that of the light.

Modification of the X-Ray Diagnosis Apparatus

[Configuration]

As illustrated in FIG. 15, in this embodiment, the X-ray diagnosis apparatus 1 includes the heat radiation part 500 that thermally connects the light source device 100 to the X-ray generator 200. The heat radiation part 500 radiates heat from the light source device 100 and the X-ray generator 200. The heat radiation part 500 may be formed of a heat radiation member such as a heat sink, a path of a cooling medium, and the like.

In this embodiment, the X-ray irradiation unit 10 includes the heat radiation part 500 that thermally connects the light source device 100 to the X-ray generator 200. Thus, it is possible to provide an X-ray irradiation unit capable of suitably radiating heat generated by the light source device 100 and the X-ray generator 200.

Fifth Embodiment of the Light Source Device

[Configuration]

Figure 16A:
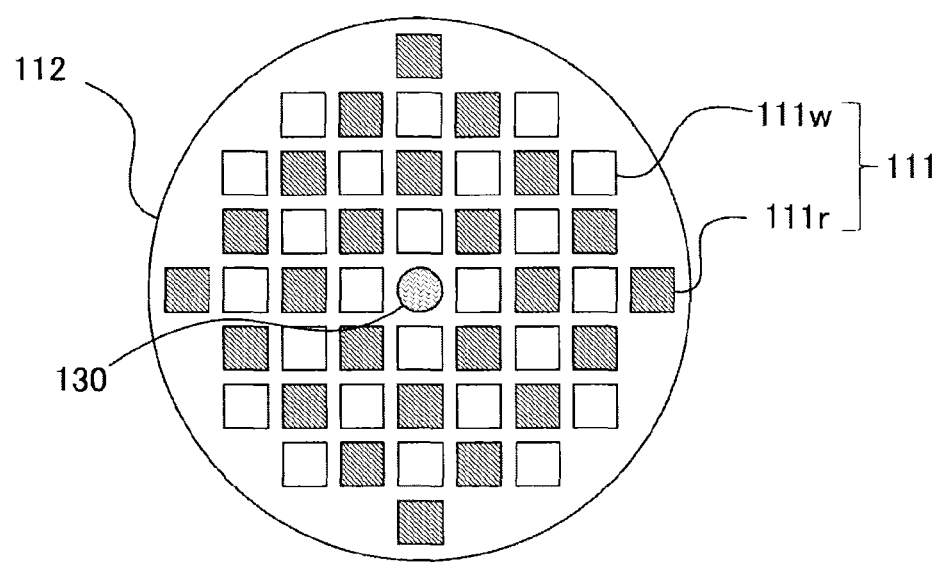
FIG. 16A is a view illustrating an example of the configuration of a light source device according to an embodiment.

In the light source device 100 of this embodiment, the light emitters 111 of the light-emitting part 110 include two or more light emitter groups that emit light of two or more different colors. Otherwise, the light source device 100 of this embodiment is of basically the same configuration as in the first embodiment. Therefore, like parts as those of the light source device of the first embodiment are described using like reference numerals. FIG. 16A is a schematic diagram illustrating a configuration in which the light emitters 111 include two light emitter groups. Light emitters 111r emit red light. On the other hand, light emitters 111w emit white light. A group of the light emitters 111 that emits light of the same color is referred to as a light emitter group.

The two or more light emitter groups are arranged point-symmetrically with respect to the center of the light-emitting surface S of the light-emitting part 110. That is, the light emitters 111 in the light emitter groups are arranged substantially uniformly without any imbalance in the light-emitting surface S of the light-emitting part 110.

As illustrated in FIG. 16B, the light source device 100 further includes a light emission control unit 600. According to the operating state of the X-ray irradiation unit, the light emission control unit 600 controls the light-emitting part 110. At this time, the light emission control unit 600 controls the light-emitting part 110 to change the light emission mode thereof. Specifically, the light emission control unit 600 controls the light-emitting part 110 so that the light emission mode varies among the fluoroscopy state, the imaging state, and the stopped state of the X-ray irradiation unit 10. The light emission mode includes emission color, emission intensity or emission time, or two or more of these. The light emission control unit 600 controls the operation of each of two or more light emitter groups. By controlling power supply state with respect to each light emitter group, the light emission control unit 600 controls the emission color and the emission intensity. The control of the emission time includes strobe light emission control for causing the light emitters 111 to repeat turning on and off the light at regular intervals. Incidentally, if the light source device 100 is applied to the X-ray diagnosis apparatus 1, the light emission control unit 600 may be included in the controller 40.

First Operation Example

Figure 17:
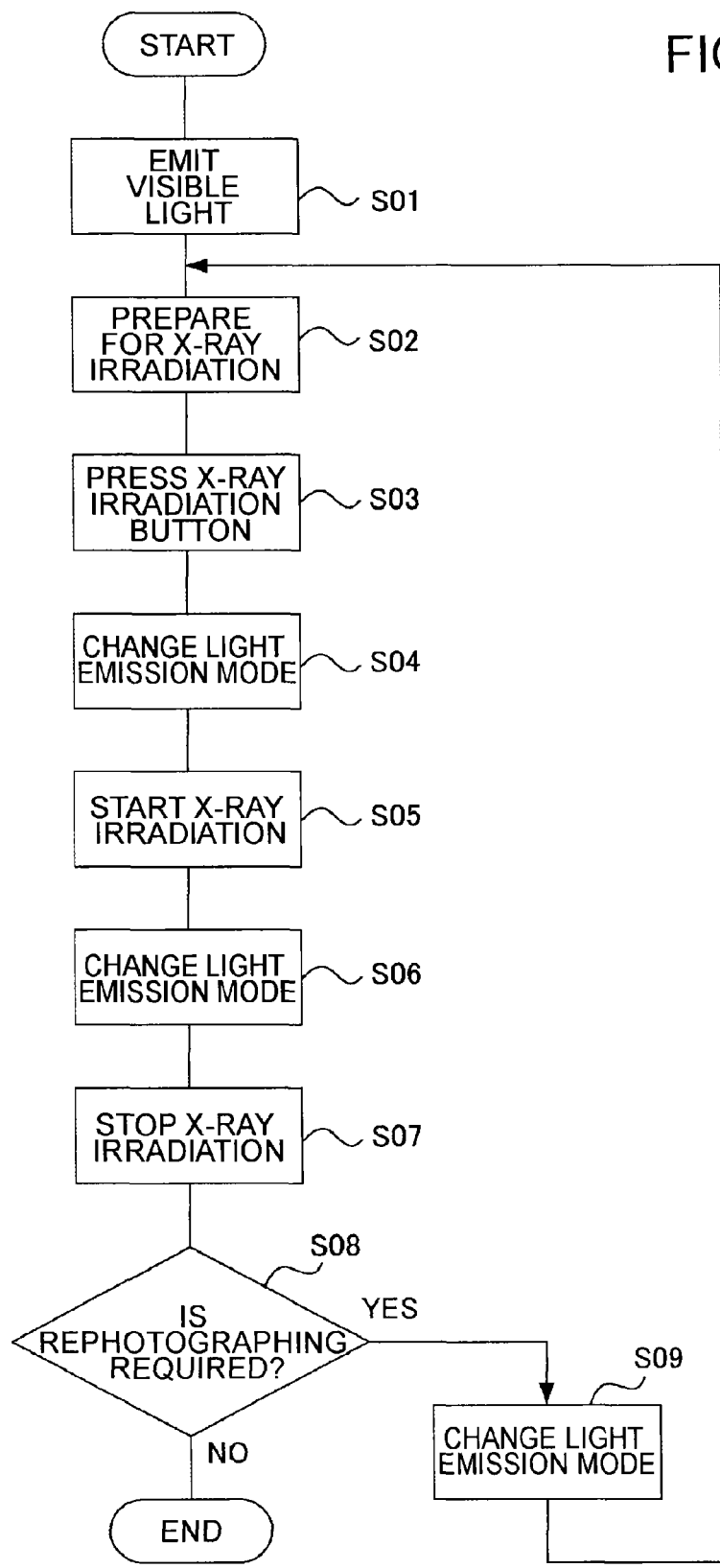
FIG. 17 is a flowchart illustrating an example of the operation of an X-ray diagnosis apparatus including a light source device according to an embodiment.

With reference to the flowchart of FIG. 17, a description is given of the first operation example in which the light source device 100 of this embodiment is applied to the X-ray diagnosis apparatus 1.

(Step S01)

When power is supplied to the light source device 100, the light-emitting part 110 emits light. At this time, the light emission control unit 600 controls power supply state for each light emitter group so that the light-emitting part 110 emits light in predetermined light emission mode. For example, the light emission control unit 600 may control the light-emitting part 110 to continuously emit white light of high intensity.

(Step S02)

The operator adjusts the irradiation field of X-rays so that the position and range thereof are suitable to the subject. At this time, the operator adjusts the X-ray irradiation field by visually checking the irradiation field of light from the light source device 100. In other words, the X-ray irradiation field is adjusted by adjusting the irradiation field of light.

(Step S03)

Upon completion of the adjustment of the X-ray irradiation field, the operator presses an X-ray irradiation button (not illustrated).

(Step S04)

When the X-ray irradiation button is pressed, the light emission control unit 600 controls the power supply state for each light emitter group to change the light emission mode of the light-emitting part 110. For example, the light emission control unit 600 may change the light emission mode so that the light-emitting part 110 continuously emits red light of low intensity.

(Step S05)

After a lapse of predetermined time from when the X-ray irradiation button is pressed, the X-ray generator 200 generates X-rays, and thus X-ray irradiation starts. At this time, the X-rays are irradiated in the irradiation field adjusted in step S02.

(Step S06)

After the start of the X-ray irradiation, the light emission control unit 600 controls the power supply state for each light emitter group to change the light emission mode of the light-emitting part 110. For example, the light emission control unit 600 may change the light emission mode so that the light-emitting part 110 emits flashing white light of high intensity (strobe light emission). When the subject moves during the flashing light emission (strobe light emission) by the light-emitting part 110, the operator can easily view the movement frame by frame.

(Step S07)

The X-ray irradiation is stopped by automatic control based on a lapse of predetermined time from the start of the X-ray irradiation. The light source device 100 is turned off at this time. Note that the X-ray irradiation may be stopped in response to operation by the operator.

(Step S08)

The operator determines whether rephotographing is required based on the presence or absence of movement of the subject during the X-ray irradiation. If rephotographing is not required (No in step S08), the X-ray imaging operation ends.

(Step S09)

On the other hand, if required (Yes in step S08), rephotographing is performed. At this time, the light emission control unit 600 controls the power supply state for each light emitter group to change the light emission mode of the light-emitting part 110. For example, the light emission control unit 600 may change the light emission mode so that the light-emitting part 110 continuously emits white light of high intensity. Then, process flow loops back to step S02.

In the first operation example, step S01 corresponds to an example of "emitting light" step in the control method of the X-ray diagnosis apparatus. Further, steps S04, S06 and S09 correspond to an example of "controlling" step in the control method of the X-ray diagnosis apparatus.

Second Operation Example

Figure 18:
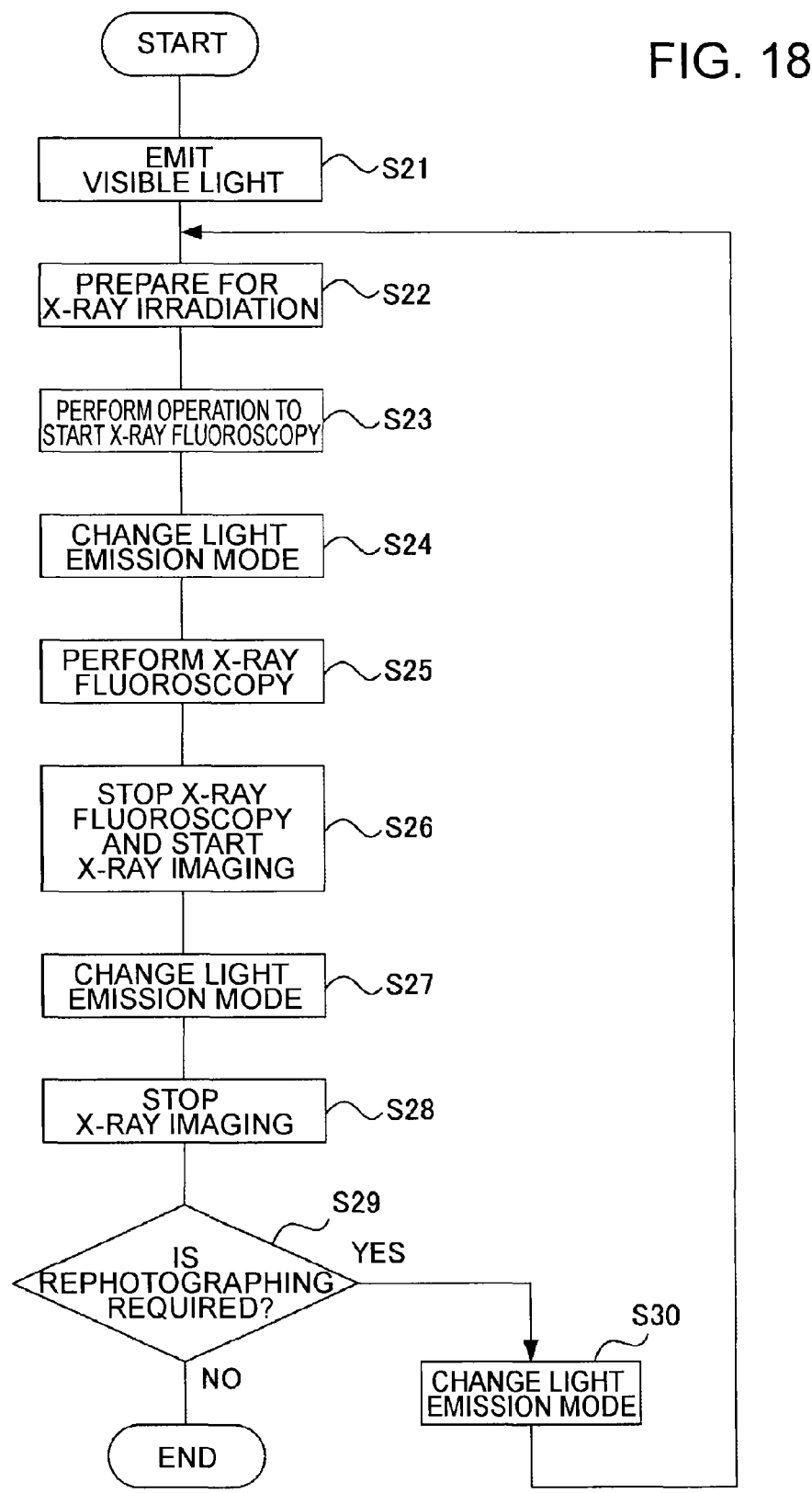
FIG. 18 is a flowchart illustrating an example of the operation of an X-ray diagnosis apparatus including a light source device according to an embodiment.

With reference to the flowchart of FIG. 18, a description is given of the second operation example in which the light source device 100 of this embodiment is applied to the X-ray diagnosis apparatus 1. This operation example includes the operation of the light emission control unit 600 for controlling the light emission mode of the light-emitting part 110 in response to the operation to start or stop the fluoroscopy state and the imaging state.

(Step S21)

When power is supplied to the light source device 100, the light-emitting part 110 emits light. At this time, the light emission control unit 600 controls power supply state for each light emitter group so that the light-emitting part 110 emits light in predetermined light emission mode. For example, the light emission control unit 600 may control the light-emitting part 110 to continuously emit white light of high intensity.

(Step S22)

The operator adjusts the irradiation field of X-rays so that the position and range thereof are suitable to the subject. At this time, the operator adjusts the X-ray irradiation field by visually checking the irradiation field of light from the light source device 100. In other words, the X-ray irradiation field is adjusted by adjusting the irradiation field of light.

(Step S23)

Upon completion of the adjustment of the X-ray irradiation field, the operator performs the operation to start the fluoroscopy state using the fluoroscopy switch 71.

(Step S24)

When the fluoroscopy switch 71 receives the operation to start the fluoroscopy state, the light emission control unit 600 controls the power supply state for each light emitter group to change the light emission mode of the light-emitting part 110. For example, the light emission control unit 600 may change the light emission mode so that the light-emitting part 110 continuously emits red light of low intensity.

(Step S25)

When a predetermined time has elapsed after the fluoroscopy switch 71 receives the operation to start the fluoroscopy state, the X-ray generator 200 generates X-rays for X-ray fluoroscopy, and thus the fluoroscopy state starts. At this time, the X-rays are irradiated in the irradiation field adjusted in step S22. With the start of the fluoroscopy state, the light emission control unit 600 controls the power supply state for each light emitter group to change the light emission mode of the light-emitting part 110. For example, the light emission control unit 600 may change the light emission mode so that the light-emitting part 110 emits flashing white light of higher intensity than the light in step S24 (strobe light emission). When the subject moves during the flashing light emission (strobe light emission) by the light-emitting part 110, the operator can easily view the movement frame by frame.

(Step S26)

The operator performs the operation to stop the fluoroscopy state using the fluoroscopy switch 71, and also the operation to start the imaging state using the imaging switch 72.

(Step S27)

When a predetermined time has elapsed after the fluoroscopy switch 71 receives the operation to stop the fluoroscopy state and the imaging switch 72 receives the operation to start the imaging state, the X-ray generator 200 generates X-rays for X-ray imaging, and thus the imaging state starts. At this time, the X-rays are irradiated in the irradiation field adjusted in step S22. With the start of the imaging state, the light emission control unit 600 controls the power supply state for each light emitter group to change the light emission mode of the light-emitting part 110. For example, the light emission control unit 600 may change the emission intensity of the light-emitting part 110 so that the light-emitting part 110 emits flashing white light of higher intensity than the light in step S25 (strobe light emission). The change of the emission intensity allows the operator to easily identify the fluoroscopy state and the imaging state.

(Step S28)

When the imaging switch 72 receives the operation to stop the imaging state, the X-ray generator 200 stops generating X-rays, and thus the imaging state is stopped. At this time, the light source device 100 is turned off. Note that the imaging state may be stopped by automatic control based on a lapse of predetermined time from the start of the imaging state.

(Step S29)

The operator determines whether rephotographing is required based on the presence or absence of movement of the subject during the imaging state. If rephotographing is not required (No in step S29), the X-ray imaging operation ends.

(Step S30)

On the other hand, if required (Yes in step S29), rephotographing is performed. At this time, the light emission control unit 600 controls the power supply state for each light emitter group to change the light emission mode of the light-emitting part 110. For example, the light emission control unit 600 may change the light emission mode so that the light-emitting part 110 continuously emits white light of high intensity. Then, process flow loops back to step S22.

In the second operation example, step S21 corresponds to an example of "emitting light" step in the control method of the X-ray diagnosis apparatus. Further, steps S24, S25, S27 and S30 correspond to an example of "controlling" step in the control method of the X-ray diagnosis apparatus.

In this embodiment, the light emitters 111 include two or more light emitter groups that emit light of two or more different colors. The two or more light emitter groups are arranged point-symmetrically with respect to the center of the light-emitting surface S of the light-emitting part 110. The light source device 100 further includes the light emission control unit 600 that controls the operation of each of the two or more light emitter groups. In the X-ray diagnosis apparatus 1 provided with the light source device 100 of this embodiment, the light emission control unit 600 controls the light-emitting part 110 according to the operating state of the X-ray irradiation unit 10. At this time, the light emission control unit 600 controls the light-emitting part 110 so that the light emission mode varies among the fluoroscopy state, the imaging state, and the stopped state. With this, the operation of the light source device can be controlled correspondingly to the operation procedure of the X-ray diagnosis apparatus that uses the light source device 100. Thus, it is possible to provide the light source device 100 which allow the operator to easily grasp the work progress.

If the light irradiation part 130 includes a fluorescent material, the light emission control unit 600 may control the emission intensity or the emission time of the light-emitting part 110, or both, according to the operating state of the X-ray irradiation unit 10.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus, comprising:
    an X-ray irradiator configured to emit X-rays to a subject;
    a light source device including
        a light-emitting part that forms a planar light-emitting surface configured to emit light,
        a reflective part having a reflective surface to collect the light and including a first reflective part having a first reflective surface, the first reflective part being arranged such that focus of the first reflective surface is located on the light-emitting surface, and
        a light irradiation part substantially located at a position of the focus where the light is collected by the reflective part and configured to emit the light as output light indicating an irradiation field of the X-rays; and
    a light emission control unit configured to control the light-emitting part according to operating state of the X-ray irradiator.

2. The X-ray diagnosis apparatus of claim 1, wherein the light irradiation part is configured to emit the light as the output light of uniform brightness.

3. The X-ray diagnosis apparatus of claim 1, wherein the light irradiation part includes a diffusion filter configured to diffuse the light to emit the output light.

4. The X-ray diagnosis apparatus of claim 1, wherein the light emission control unit is configured to control the light-emitting part to change light emission mode including any one or two or more of emission color, emission intensity, and emission time of the light.

5. The X-ray diagnosis apparatus of claim 4, wherein
    the operating stale includes stopped state where X-ray irradiation is stopped, fluoroscopy state where the X-rays are irradiated for X-ray fluoroscopy, and imaging state where the X-rays are irradiated for X-ray imaging, and
    the light emission control unit is configured to control the light-emitting part so that the light emission mode varies among the stopped state, the fluoroscopy state, and the imaging state.

6. The X-ray diagnosis apparatus of claim 5, further comprising an operation unit configured to receive operation related to the operating state, wherein
    the light emission control unit is configured to control the light-emitting part to change the light emission mode in response to the operation.

7. The X-ray diagnosis apparatus of claim 6, wherein
    the operation unit includes
        a fluoroscopy switch configured to receive operation to start or stop the fluoroscopy state, and
        an imaging switch configured to receive operation to start or stop the imaging state, and
    when the fluoroscopy switch or the imaging switch receives the operation, the light emission control unit controls the light-emitting part in response to the operation.

8. The X-ray diagnosis apparatus of claim 1, wherein the light-emitting part includes a semiconductor laser or a light-emitting diode configured to emit the light having directivity.

9. The X-ray diagnosis apparatus of claim 1, wherein
    the light-emitting part includes a plurality of semiconductor lasers or the light-emitting diodes that are arranged point-symmetrically with respect to center of the light-emitting surface, and
    the first reflective part being arranged such that an axis of the first reflective surface is perpendicular to the light-emitting surface.

10. The X-ray diagnosis apparatus of claim 9, wherein
    the light-emitting part includes two or more groups of the semiconductor lasers or two or more groups of the light-emitting diodes to emit light of two or more different colors,
    the two or more groups of the semiconductor lasers or the two or more groups of the light-emitting diodes are arranged point-symmetrically with respect to the center of the light-emitting surface, and
    the light emission control unit configured to control operation of each of the groups of the semiconductor lasers or each of the groups of the light-emitting diodes.

11. The X-ray diagnosis apparatus of claim 9, wherein
    in the light-emitting part, the semiconductor lasers or the light-emitting diodes are arranged discretely to form the light-emitting surface, and
    the reflective part includes a second reflective part located between the semiconductor lasers or the light-emitting diodes, and having a second reflective surface, at least part of which is formed in a curved shape, having ridges in concentric circles.

12. The X-ray diagnosis apparatus of claim 9, further comprising a second heat radiation part that is located between an outer edge of the light-emitting part and an outer edge of the first reflective part.

13. The X-ray diagnosis apparatus of claim 9, further comprising a third heat radiation part arranged point-symmetrically as part of the first reflective part, and configured to radiate heat through the first reflective part.

14. The X-ray diagnosis apparatus of claim 1, wherein the light irradiation part includes a fluorescent material that emits light as excited by the light.

15. The X-ray diagnosis apparatus of claim 1, further comprising a first heat radiation part that is located opposite the planar light-emitting surface in the light-emitting part.

16. The X-ray diagnosis apparatus of claim 1, further comprising a positive lens in a downstream of the light irradiation part.

17. The X-ray diagnosis apparatus of claim 1, wherein
the light-emitting part includes a plurality of semiconductor lasers or the light-emitting diodes that are arranged point-symmetrically with respect to center of the light-emitting surface,
the first reflective surface is parabolic,
the first reflective part is arranged such that an axis of the first reflective surface is perpendicular to the light-emitting surface,
in the light-emitting part, the semiconductor lasers or the light-emitting diodes are arranged discretely to form the light-emitting surface,
the reflective part includes a second reflective part located between the semiconductor lasers or the light-emitting diodes, and having a second reflective surface, at least part of which is formed in a curved shape, having ridges in concentric circles, and
the light irradiation part includes a fluorescent material that emits light as excited by the light.

* * * * *